(12) United States Patent
Doherty et al.

(10) Patent No.: US 6,265,382 B1
(45) Date of Patent: Jul. 24, 2001

(54) DIPEPTIDE INHIBITORS OF PROTEIN FARNESYLTRANSFERASE

(75) Inventors: Annette Marian Doherty; Daniele Marie Leonard; Dennis Joseph McNamara, all of Ann Arbor; Kevon Ray Shuler, Chelsea, all of MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/331,876
(22) PCT Filed: Apr. 2, 1998
(86) PCT No.: PCT/US98/06482
§ 371 Date: Jun. 28, 1999
§ 102(e) Date: Jun. 28, 1999
(87) PCT Pub. No.: WO98/46625
PCT Pub. Date: Oct. 22, 1998

Related U.S. Application Data
(60) Provisional application No. 60/043,492, filed on Apr. 11, 1997.

(51) Int. Cl.[7] .................................................. C07K 5/06
(52) U.S. Cl. ........................................... 514/19; 548/344
(58) Field of Search ................................ 514/19; 548/344

(56) References Cited

FOREIGN PATENT DOCUMENTS

96/00736 * 1/1996 (WO) .
97/44350 * 11/1997 (WO) .

* cited by examiner

*Primary Examiner*—Christopher S. F. Low
*Assistant Examiner*—David Lukton
(74) *Attorney, Agent, or Firm*—Charles W. Ashbrook

(57) ABSTRACT

The present invention provides compounds having the structure represented by formula (I). Also provided is a method of treating cancer, restenosis, atherosclerosis, or psoriasis or preventing restenosis, and a pharmaceutical composition comprising a compound of formula (I).

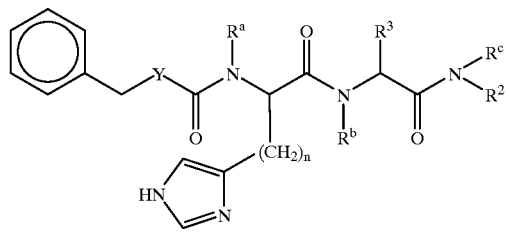

13 Claims, No Drawings

DIPEPTIDE INHIBITORS OF PROTEIN FARNESYLTRANSFERASE

This appln claims benefit of provisional appln 60/043,492, Apr. 11, 1997. This appln is a 371 of PCT/US98/06482, Apr. 2, 1998.

FIELD OF THE INVENTION

The present invention relates to compounds that can be used in the medicinal field to treat, prophylactically or otherwise, uncontrolled or abnormal proliferation of human tissues. Specifically, the present invention relates to compounds that inhibit the farnesyl transferase enzyme, which has been determined to activate ras proteins that in turn activate cellular division and are implicated in cancer, restenosis, atherosclerosis, and psoriasis.

BACKGROUND OF THE INVENTION

Ras protein (or p21) has been examined extensively because mutant forms are found in 20% of most types of human cancer and greater than 50% of colon and pancreatic carcinomas (Gibbs J. B., Cell, 1991;65:1, Cartwright T., et al., Chimica. Oggi., 1992;10:26). These mutant ras proteins are deficient in the capability for feedback regulation that is present in native ras, and this deficiency is associated with their oncogenic action since the ability to stimulate normal cell division cannot be controlled by the normal endogenous regulatory cofactors. The recent discovery that the transforming activity of mutant ras is critically dependent on posttranslational modifications (Gibbs J., et al., Microbiol. Rev., 1989;53:171) has unveiled an important aspect of ras function and identified novel prospects for cancer therapy.

In addition to cancer, there are other conditions of uncontrolled cellular proliferation that may be related to excessive expression and/or function of native ras proteins. Postsurgical vascular restenosis is such a condition. The use of various surgical revascularization techniques such as saphenous vein bypass grafting, endarterectomy, and transluminal coronary angioplasty are often accompanied by complications due to uncontrolled growth of neointimal tissue, known as restenosis. The biochemical causes of restenosis are poorly understood and numerous growth factors and protooncogenes have been implicated (Naftilan A. J., et al., Hypertension, 1989;13:706 and J. Clin. Invest., 83:1419; Gibbons G. H., et al., Hypertension, 1989;14:358; Satoh T., et al., Molec. Cell. Biol., 1993;13:3706). The fact that ras proteins are known to be involved in cell division processes makes them a candidate for intervention i many situations where cells are dividing uncontrollably. In direct analogy to the inhibition of mutant ras related cancer, blockade of ras dependent processes has the potential to reduce or eliminate the inappropriate tissue proliferation associated with restenosis, particularly in those instances where normal ras expression and/or function is exaggerated by growth stimulatory factors.

Ras functioning is dependent upon the modification of the proteins in order to associate with the inner face of plasma membranes. Unlike other membrane-associated proteins, ras proteins lack conventional transmembrane or hydrophobic sequences and are initially synthesized in a cytosol soluble form. Ras protein membrane association is triggered by a series of postranslational processing steps that are signaled by a carboxyl terminal amino acid consensus sequence that is recognized by protein farnesyl transferase (PFT). This consensus sequence consists of a cysteine residue located four amino acids from the carboxyl terminus, followed by two lipophilic amino acids, and the C-terminal residue. The sulfhydryl group of the cysteine residue is alkylated by farnesylpyrophosphate in a reaction that is catalyzed by protein farnesyl transferase. Following prenylation, the C-terminal three amino acids are cleaved by an endoprotease and the newly exposed alpha-carboxyl group of the prenylated cysteine is methylated by a methyl transferase. The enzymatic processing of ras proteins that begins with farnesylation enables the protein to associate with the cell membrane. Mutational analysis of oncogenic ras proteins indicates that these posttranslational modifications are essential for transforming activity. Replacement of the consensue sequence systeine residue with other amino acids gives a ras protein that is no longer farnesylated, fails to migrate to the cell membrane and lacks the ability to stimulate cell proliferation (Hancock J. F., et al., Cell, 1989;57:1617, Schafer W. R., et al., Science, 1989;245:379, Casey P. J., Proc. Natl. Acad. Sci. USA, 1989;86:8323).

Recently, protein farnesyl transferases (PFTs), also referred to as farnesyl proteintransferases (FPTs) have been identified, and a specific PFT from rat brain was purified to homogeneity (Reiss Y., et al., Biochem. Soc. Trans., 1992;20:487–88). The enzyme was characterized as a heterodimer composed of one alpha-subunit (49kDa) and one beta-subunit (46kDa), both of which are required for catalytic activity. High level expression of mammalian PFT in a baculovirus system and purification of the recombinant enzyme in active form has also been accomplished (Chen, W. J., et al., J. Biol. Chem., 1993;268:9675).

In light of the foregoing, the discovery that the function of oncogenic ras proteins is critically dependent on their posttranslational processing provides a means of cancer chemotherapy through inhibition of the processing enzymes. The identification and isolation of a protein farnesyl transferase that catalyzes the addition of a farnesyl group to ras proteins provides a promising target for such intervention. Ras farnesyl transferase inhibitors have been shown to have anticancer activity in several recent articles.

Ras inhibitor agents act by inhibiting farnesyl transferase, the enzyme that anchors the protein product of the ras gene to the cell membrane. The role of the ras mutation in transducing growth signals within cancer cells relies on the protein being in the cell membrane, so with farnesyl transferase inhibited, the ras protein will stay in the cytosol and be unable to transmit growth signals: these facts are well-known in the literature.

A peptidomimetic inhibitor of farnesyl transferase B956 and its methyl ester B1086 at 100 mg/kg have been shown to inhibit tumor growth by EJ-1 human bladder carcinoma, HT1080 human fibrosarcoma, and human colon carcinoma xenografts in nude mice (Nagasu, T., et al., Cancer Res., 1995;55:5310–5314). Furthermore, inhibition of tumor growth by B956 has been shown to correlate with inhibition of ras posttranslational processing in the tumor. Other ras farnesyl transferase inhibitors have been shown to specifically prevent ras processing and membrane localization and are effective in reversing the transformed phenotype of mutant ras containing cells (Sepp-Lorenzino L., et al., Cancer Res., 1995;55:5302–5309).

In another report (Sun J., et al., Cancer Res., 1995;55:4243–4247), a ras farnesyl transferase inhibitor FT1276 has been shown to selectively block tumor growth in nude mice of a human lung carcinoma with K-ras mutation and p53 deletion. In yet another report, daily administration of a ras farnesyl transferase inhibitor L-744,832 caused tumor regression of mammary and salivary carcinomas in ras transgenic mice (Kohl et al., *Nature Med.*, 1995;1(8):792–748). Thus, ras farnesyl transferase inhibitors have benefit in certain forms of cancer, particularly those dependent on oncogenic ras for their growth. However, it is well-known that human cancer is often manifested when several mutations in important genes occur, one or more of which may be responsible for controlling growth and metastases. A single mutation may not be enough to sustain growth and only after two or three mutations occur, tumors can develop and grow. It is therefore difficult to determined which of these mutations may be primarily driving the growth in a particular type of cancer. Thus, ras farnesyl transferase inhibitors can have therapeutic utility in tumors not solely dependent on oncogenic forms of ras for their growth. For example, it has been shown that various ras FT-inhibitors have antiproliferative effects in vivo against tumor lines with either wild-type or mutant ras (Sepp-Lorenzino, surpa). In addition, there are several ras-related protein that are prenylated. Proteins such as R-Ras2/ TC21 are ras-related proteins that are prenylated in vivo by both farnesyl transferase and geranylgeranyl transferase I (Carboni, et al., *Oncogene,* 1995;10:1905–1913). Therefore, ras farnesyl transferase inhibitors could also block the prenylation of the above proteins and therefore would then be useful in inhibiting the growth of tumors driven by other oncogenes.

With regard to restenosis and vascular proliferative diseases, it has been shown that inhibition of cellular ras prevents smooth muscle proliferation after vascular injury i vivo (Indolfi C., et al., *Nature Med.,* 1995;1(6):541–545). This report definitively supports a role for farnesyl transferase inhibitors in this disease, showing inhibition of accumulation and proliferation of vascular smooth muscle.

SUMMARY OF THE INVENTION

Provided by the present invention are compounds having the Formula I

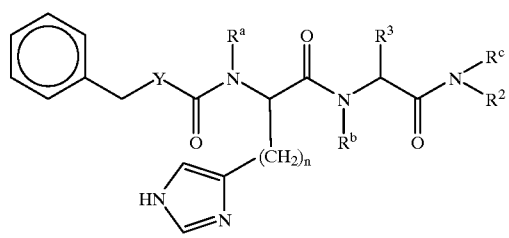

wherein $R^a$, $R^b$, and $R^c$ are each independently $C_1$–$C_6$ alkyl or hydrogen;

$R^d$, $R^e$, $R^f$, and $R^g$ are each independently $C_1$–$C_6$ alkyl, hydrogen, or phenyl;

Y is —O—, —NH—, or —N($C_1$–$C_6$ alkyl)—

$R^3$ is —(CH$_2$)$_n$-phenyl,

—(CH$_2$)$_n$-heteroaryl, or

—(CH$_2$)$_n$-substituted phenyl;

$R^2$ is 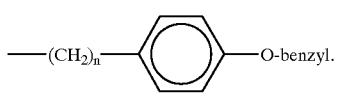, or 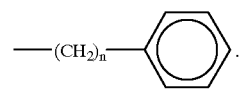;

$R^4$ is aryl, substituted aryl, or $C_1$–$C_6$ alkyl; and each n is independently 0 to 5, m is 2 to 4, and the pharmaceutically acceptable salts, and prodrugs thereof.

In a preferred embodiment of Formula I, Y is —O—.

In another preferred embodiment of Formula I,

Y is —NH— or —N(CH$_3$)—.

In another preferred embodiment of Formula I, $R^a$ is hydrogen, $R^b$ is methyl, and $R^c$ is hydrogen.

In another preferred embodiment of Formula I, $R^3$ is

—(CH$_2$)$_n$—C$_6$H$_4$—O-benzyl.

In another preferred embodiment of Formula I, $R^3$ is

—(CH$_2$)$_n$—C$_6$H$_5$.

In another preferred embodiment of Formula I, $R^2$ is —CH$_2$CH$_2$— phenyl or —CH$_2$CH$_2$-substituted phenyl.

In another preferred embodiment of Formula I, $R^2$ is —CH(H)—C(CH$_3$)$_2$-phenyl, —CH(H)—C(CH$_3$)$_2$-substituted phenyl, —CH(CH$_3$)—CH(H)-phenyl, or —CH(CH$_3$)—CH(H)-substituted phenyl.

In another preferred embodiment of Formula I,

—CH(H)—C(phenyl)(CH$_2$)$_m$ or —CH(H)—C(substituted phenyl)(CH$_2$)$_m$.

In another preferred embodiment of Formula I, $R^3$ is —(CH$_2$)$_n$-C$_1$–C$_6$ alkyl.

In another preferred embodiment of Formula I, R³ is

In a more preferred embodiment, the present invention provides the following compounds:

[S—(R*,R*)]-[1-{[2-(4-Benzyloxy-Phenyl)-1-phenethylcarbamoyl-ethyl]-methyl-carbamoyl}-2-(1H-imidazol-4-yl)-ethyl]-carbamic acid benzyl ester;

[S—(R*,R*)]-[1-{[2-(4-Benzyloxy-phenyl)-1-(2-methyl-2-phenyl-propylcarbamoyl)-ethyl]-methyl-carbamoyl}-2-(1H-imidazol-4-yl)-ethyl]-carbamic acid benzyl ester;

[S—(R*,R*)]-[2-(1H-Imidazol-4-yl)-1-(methyl-{1-(2-methyl-2-phenyl-propylcarbamoyl)-2-[4-(pyridin-2-ylmethoxy)-phenyl]-ethyl}-carbamoyl)-ethyl]-carbamic acid benzyl ester;

[S—(R*,R*)]-2-(3-Benzyl-3-methyl-ureido)—N—[2-(4-benzyloxy-phenyl)-1-(2-methyl-2-phenyl-propyl-carbamoyl)-ethyl]-3-(1H-imidazol-4-yl)—N—methyl-propionamide;

[S—(R*,R*)]-[1-{[2-(4-Benzyloxy-phenyl)-1-[(1-phenyl-cyclobutylmethyl)-carbamoyl]-ethyl}-methyl-carbamoyl)-2-(3H-imidazol-4-yl)-ethyl]-carbamic acid benzyl ester;

[S—(R*,R*)]-[2-(3H-Imidazol-4-yl)-1-{methyl-[1-(2-methyl-2-phenyl-propylcarbamoyl)-2-phenyl-ethyl]-carbamoyl}-ethyl-carbamic acid benzyl ester; and

[S—(R*,R*)]-[2-(3H-Imidazol-4-yl)-1-{methyl-3-methyl-1-(2-methyl-2-phenyl-propylcarbamoyl)-butyl]-carbamoyl}-ethyl-carbamic acid benzyl ester.

In another more preferred embodiment, the present invention provides the following compounds:

[S—(R*,R*)]-[1-({2-(4-Benzyloxy-phenyl)-1-[2-(2-fluoro-phenyl)-ethyl-carbamoyl]-ethyl}-methyl-carbamoyl)-2-(3H-imidazol-4-yl)-ethyl]-carbamic acid benzyl ester;

[S—(R*,R*)]-[1-{[2-(4-Benzyloxy-phenyl)-1-(2-pyridin-2-yl-ethyl-carbamoyl)-ethyl]-methyl-carbamoyl}-2-(3H-imidazol-4-yl)-ethyl]-carbamic acid benzyl ester;

[S—(R*,R*)]-[1-{[2-(4-Benzyloxy-phenyl)-1-(2,2-diphenyl-ethylcarbamoyl)-ethyl]-methyl-carbamoyl}-2-(3H-imidazol-4-yl)-ethyl]-carbamic acid benzyl ester;

[S—(R*,R*)]-[1-{[2-(4-Benzyloxy-phenyl)-1-(2-phenyl-propylcarbamoyl)-ethyl]-methyl-carbamoyl}-2-(3H-imidazol-4-yl)-ethyl]-carbamic acid benzyl ester;

[S—(R*,R*)]-(2-(3H-Imidazol-4-yl)-1-{methyl-[3-methyl-1-(2-methyl-2-phenyl-proplcarbamoyl)-butyl]-carbamoyl}-ethyl)-carbamic acid benzyl ester;

[S—(R*,R*)]-[1-{[2-(4-Benzyloxy-phenyl)-1-(1-mehyl-2-phenyl-ethylcarbamoyl)-ethyl]-methyl-carbamoyl}-2-(3H-imidazol-4-yl)ethyl]-carbamic acid benzyl ester;

[S—(R*,R*)]-[1-({2-(4-Benzyloxy-phenyl)-1-[(1-phenyl-cyclopropyl-methyl)-carbamoyl]-ethyl}-methyl-carbamoyl)-2-(3H-imidazol-4-yl)-ethyl]-carbamic acid benzyl ester;

[S—(R*,R*)]-[1-{[2-(4-Chloro-phenyl)-1-(2-methyl-2-phenyl-propylcarbamoyl)-ethyl]-methyl-carbamoyl}-2-(3H-imidazol-4-yl)-ethyl]-carbamic acid benzyl ester;

[S—(R*,R*)]-2-(3-Benzyl-ureido)3-(3H-imidazol-4-yl)—N-methyl-N—{1-(2-methyl-propyl-carbamoyl)-2-[4-(pyridin-4-ylmethoxy)-phenyl]-ethyl}-propionamide;

[S—(R*,R*)]-[1-{[2-(4-Benzyloxy-phenyl)-1-(1-methyl-2-phenyl-ethylcarbamoyl)-ethyl]-methyl-carbamoyl}-2-(3H-imidazol-4-yl)-ethyl]-carbamic acid benzyl ester;

[S—(R*,R*)]-(2-(3H-Imidazol-4-yl)-1-{methyl-[1-(2-methyl-2-phenyl-propylcarbamoyl)-2-p-tolyl-ethyl]-carbamoyl}-ethyl)-carbamic acid benzyl ester;

[S—(R*,R*)]-(2-(3H-Imidazol-4-yl)-1-{[2-(4-methoxy-phenyl)-1-(2-methyl-2-phenyl-propylcarbamoyl)-ethyl]-methyl-carbamoyl}-ethyl)-carbamic acid benzyl ester;

[S—(R*,R*)]-2-(3-Benzyl-ureido)-3-(3H-imidazol-4-yl)—N-methyl-N—[1-(2-methyl-2-phenyl-propylcarbamoyl)-2-phenyl-ethyl]-propionamide; and

[S—(R*,R*)]-[1-[(2-(4-Benzyloxy-phenyl)-1-{[1-(2-fluoro-phenyl)-cyclopropylmethyl]-carbamoyl}ethyl)-methyl-carbamoyl]-2-(3H-imidazol-4-yl)-ethyl]-carbamic acid benzyl ester.

Also provided is a method of treating cancer, the method comprising administering to a patient havig a cancer a therapeutically effective amount of a compound of Formula I.

Also provided is a method of treating or preventing restenosis, the method comprising administering to a patient having restenosis or at risk of having restenosis a therapeutically effective amount of a compound of Formula I.

Also provided is a method of treating atherosclerosis, the method comprising administering to a patient having atherosclerosis a therapeutically effective amount of a compound of Formula I.

Also provided is a method of treating psoriasis, the method comprising administering to a patient having psoriasis a therapeutically effective amount of a compound of Formula I.

Also provided is a pharmaceutical composition that comprises a compound of Formula I.

DETAILED DESCRIPTION OF THE INVENTION

The present invention provides compounds having the Formula I.

I wherein $R^a$, $R^b$, and $R^c$ are each independently $C_1$–$C_6$ alkyl or hydrogen;

$R^d$, $R^e$, $R^f$, and $R^g$ are each independently $C_1$–$C_6$ alkyl, hydrogen, or phenyl;

Y is —O—, —N(H)—, or —N($C_1$–$C_6$ alkyl)—;

R³ is —(CH₂)ₙ-phenyl, 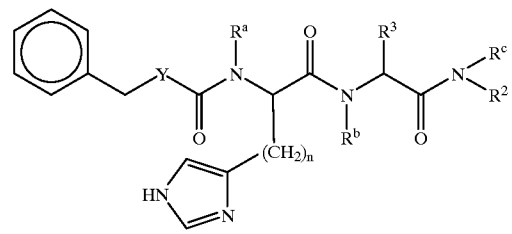

-continued

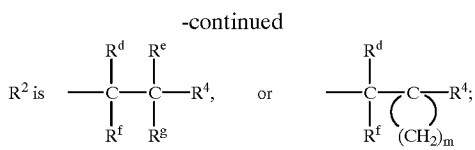

R⁴ is aryl, substituted aryl, or $C_1$–$C_6$ alkyl; and each n is independently 0 to 5, m is 2 to 4, and the pharmaceutically acceptable salts, ad prodrugs thereof.

The term "aklyl" means a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like.

The alkyl groups of the present invention include substituted alkyl groups. Examples of suitable substituents include, but are not limited to, halogen, —$OC_1$–$C_6$ alkyl, —$SC_1$–$C_6$ aklyl, —$CF_3$, —$NO_2$, —CN, phenyl, —OH, —SH, —$NH_2$, —$NHC_1$–$C_6$ aklyl, or —$N(C_1$–$C_6$ alkyl)$_2$.

The term "aryl" means an aromatic ring which is a phenyl, 5-fluorenyl, 1-naphthyl, or 2-naphthyl group, unsubstituted or substituted by 1 to 3 substituents selected from alkyl, phenyl, O-phenyl, O-alkyl, and S-alkyl, OH, SH, F, Cl, Br, I, $CF_3$, $NO_2$, $NH_2$, $NHCH_3$, $N(CH_3)_2$, NHCO-alkyl, $(CH_2)_m$$CO_2$H, $NHC_1$–$C_6$ alkyl, $N(C_1$–$C_6$ alkyl)$_2$, $(CH_2)_m$$CO_2$-alkyl, $(CH_2)_m$$SO_3$H, $(CH_2)_m$$PO_3$$H_2$, $(CH_2)_m$$PO_3$(alkyl)$_2$, $(CH_2)_m$$SO_2$$NH_2$, and $(CH_2)_m$$SO_2$NH-alkyl wherein alkyl is defined as above and m=0, 1, 2, or 3.

The term "heteroaryl" means a heteroaromatic ring which is a 2- or 3-thienyl, 2- or 3-furanyl, 2- or 3-pyrrolyl, 2-, 3-, or 4-pyridyl, imidazolyl, 2-, 3-, 4-, 5-, 6-, or 7-indoxyl group, unsubstituted or substituted by 1 or 2 substituents from the group of substituents described above for aryl.

The symbol "-" means a bond.

The term "patient" means all animals including humans. Examples of patients include humans, cows, dogs, cats, goats, sheep, and pigs.

A "therapeutically effective amount" is an amount of a compound of the present invention that when administered to a patient ameliorates a symptom of restenosis, cancer, atherosclerosis, or psoriasis, or prevents restenosis. A therapeutically effective amount of a compound of the present invention can be easily determined by one skilled in the art by administering a quantity of a compound to a patient and observing the result. In addition, those skilled in the art are familiar with identifying patients having cancer, restenosis, atherosclerosis, or psoriasis, or who are at risk of having restenosis.

The term "cancer" includes, but is not limited to, the following cancers:

breast;
ovary;
cervix;
prostate;
testis;
esophagus;
glioblastoma;
neuroblastoma;
stomach;
skin, keratoacanthoma;
lung, epidermoid carcinoma, large cell carcinoma, adenocarcinoma;
bone;
colon, adenocarcinoma, adenoma;
pancreas, adenocarcinoma;
thyroid, follicular carcinoma, undifferentiated carcinoma, papillary carcinoma;
seminoma;
melanoma;
sarcoma;
bladder carcinoma;
uterine;
liver carcinoma and bilary passages;
kidney carcinoma;
myeloid disorders;
lymphoid disorders, Hodgkins, hairy cells; buccal cavity and pharynx (oral), lip, tongue, mouth, pharynx;
small intestine;
colon-rectum, large intestine, rectum;
brain and central nervous system; and
leukemia.

The term "pharmaceutically acceptable salts, and prodrugs" as used herein refers to those carboxylate salts, amino acid addition salts, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free-base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, naphtholate mesylate, glucoheptonate, lactobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge, S. M. et al., "Pharmaceutical Salts," *J. Pharm. Sci.,* 1977;66:1–19 which is incorporated herein by reference.)

The term "prodrug" refers to compounds that are rapidly transformed in vivo to yield the parent compound of the above formulae, for example, by hydrolysis in blood. A through discussion is provided in Higuchi, T. and Stella, V., "Pro-drugs as Novel Delivery Systems," Vol 14 of the A.C.S. Symposium Series, and in *Bioreversible Carriers in Drug Design*, ed. Edward, B. Roche, American Pharmaceutical Association and Pergamon Press, 1989, both of which are hereby incorporated by reference.

The compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powder, ointments, or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile-injectable solutions or dispersions. Examples of suitable aqueous and nonaqueous carriers, diluents, solvents, or vehicles include water, ethanol, polyols (propyleneglycol, polyethyleneglycol, glycerol, and the like), Cremophor EL (a derivative of castor oil and ethylene oxide; purchased from Sigma Chemical Co., St. Louis, Mo.) and suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example agar—agar, calcium carbonate, potato or tapioca starch, alginic acid, certain complex silicates, and sodium carbonate, (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and other well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, Cremophor EL (a derivative of castor oil and ethylene oxide; purchased from Sigma Chemical Co., St. Louis, Mo.), polyethyleneglycols and fatty acid esters of sorbitan or mixtures of these substances, and the like.

Besides such inert diluents, the compositions can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar—agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of the invention.

The compounds of the present invention can be administered to a patient at dosage levels in the range of about 0.1 to about 2,000 mg per day. For a normal human adult having a body weight of about 70 kg, a dosage in the range of about 0.01 to about 100 mg/kg of body weight per day is preferable. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

The compounds of the present invention can exist in different stereoisomeric forms by virtue of the presence of asymmetric centers in the compounds. It is contemplated that all stereoisomeric forms of the compounds as well as mixtures thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The examples presented below are intended to illustrate particular embodiments of the invention, and are not intended to limit the scope of the specification of the claims in any way.

Schemes 1 through 8 below show generally how compounds of the present invention can be synthesized.

Scheme 1 illustrates a general method by which some of these compounds can be prepared, by illustrating the synthesis of [R,-(R*,S*)]-[1-(2-benzyloxy-ethylcarbamoyl)-2-(4-benzyloxy-phenyl)-ethyl]-methyl-carbamoyl)-2-(1H-imidazol-4-yl)-ethyl]-carbamic acid benzyl ester (Example 1). Coupling of Boc-NMe-Tyr(OBn)-OH to 2-(phenylmethoxy)-ethylamine hydrochloride was carried out in ethyl acetate with dicyclohexylcarbodiimide (DCC) and 1-hydroxybenzotriazole (HOBt), as coupling agents, and triethylamine as the base. The resulting product was treated with 30% trifluoroacetic acid (TFA) in methylene chloride. H-NMe-Try(OBn)-NH-CH$_2$-CH$_2$-OBn.TFA was then coupled in methylene chloride to Cbz-DHis(Trt)-OH, with benzotriazole-1-yl-oxy-tris-pyrrolidino-phosphonium hexafluorophosphate (PyBOP) as coupling agent, and diisopropylethylamine (DIEA) as the base, followed by treatment with 50% TFA in methylene chloride to give the title compound.

2-(Phenylmethoxy)-ethylamine hydrochloride was prepared by reacting 2-ethanolamine hydrochloride with sodium, followed by benzyl chloride, in toluene. The product was isolated as the HCl salt.

Scheme 2 illustrates a general method by which some of these compounds can be prepared, by illustrating the synthesis of [S-(R*,R*)]-[1-{[2-(4-benzyloxy-phenyl)-1-phenethylcarbamoyl-ethyl]-methyl-carbamoyl}-2-(1H-imidazol-4-yl)-ethyl]-carbamic acid benzyl ester (Example 2). Coupling of Boc-NMe-Tyr(OBn)-OH to 2-phenylamine was carried out in methylene chloride:dimethylformamide (DMF) (1:1) with dicyclohexylcarbodiimide (DCC) and 1-hydroxybenzotriazole (HOBt), as coupling agents. The resulting product was treated with 25% trifluoroacetic acid (TFA) in methylene chloride. H-NMe-Tyr(OBn)-NH-CH$_2$-CH$_2$-phenyl. TFA was then coupled in methylene chloride:DMF (1:1) to Cbz-His(Trt)-OH with (O-(7-azabenzotriazol-1-yl)-1,1,3,3-tetramethyl uronium hexafluorophosphate (HATU) and 1-hydroxy-7-azabenzotriazole (HOAt) as coupling agents, and diisopropylethylamine (DIEA) as the base, followed by treatment with 50% TFA in methylene chloride to give the title compound.

Scheme 3 illustrates a general method by which some of these compounds can be prepared, by illustrating the synthesis of [S-(R*,R*)]-[1-{[2-(4-benzyloxy-phenyl)-1-(2-methyl-2-phenyl-propylcarbamoyl)-ethyl]-methyl-carbamoyl}-2-(1H-imidazol-4-yl)-ethyl]-carbamic acid benzyl ester (Example 3). Coupling of Boc-NMe-Tyr(OBn)-OH to β,β-dimethylphenethylamine hydrochloride was carried out in methylene chloride:DMF (3:1) with dicyclohexylcarbodiimide (DCC) and 1-hydroxybenzotriazole (HOBt), as coupling agents, and DIEA as the base. The resulting product was treated with 25% trifluoroacetic acid (TFA) in methylene chloride. H-NMe-Tyr(OBn)-NH-CH$_2$-C(CH$_3$)$_2$-phenyl. TFA was then coupled in methylene chloride to Cbz-His(Trt)-OH, with benzotriazole-1-yl-oxy-tris-pyrrolidino-phosphonium hexafluorophosphate (PyBOP) as coupling agent, and diisopropylethylamine (DIEA) as the base, followed by treatment with 50% TFA in methylene chloride to give the title compound.

β,β-Dimethylphenethylamine hydrochloride was obtained from benzyl cyanide, which was treated with 2 equivalents of sodium hydride in tetrahydrofuran (THF) and 2 equivalents of methyl iodide in THF, followed by hydrogenation (H$_2$, Pd/C, ammonia/(CH$_3$OH). The product was isolated as the hydrochloride salt.

Scheme 4 illustrates a general method by which some of these compounds can be prepared, by illustrating the synthesis of [S-(R*,R*)]-[2-(1H-imidazol-4-yl)- 1-(methyl)-{1-(2-methyl-2-phenyl-propylcarbamoyl)-2-[4-(pyridin-2-ylmethoxy)-phenyl]-ethyl}-carbamoyl)-ethyl]-carbamic acid benzyl ester (Example 4). Coupling of Boc-NMe-Tyr-OH to β,β-dimethylphenethylamine hydrochloride was carried out in THF with dicyclohexylcarbodiimide (DCC) and 1-hydroxybenzotriazole (HOBt), as coupling agents, and triethylamine as the base. Boc-NMe-Tyr-NH-CH$_2$-C(CH$_3$)$_2$-phenyl was dissolved in THF and treated with 2-pyridylcarbinol and triphenylphosphine followed by diethyl azodicarboxylate, under a nitrogen atmosphere. The resulting product was treated with 33% trifluoroacetic acid (TFA) in methylene chloride. H-NMe-Tyr(O-CH$_2$-(2-pyridyl))-NH-CH$_2$-C(CH$_3$)$_2$-phenyl. TFA was then coupled in methylene chloride to Cbz-His(Trt)-OH, with benzotriazole-1-yl-oxy-tris-pyrrolidino-phosphonium hexafluorophosphate (PyBOP) as coupling agent, and diisopropylethylamine (DIEA) as the base, followed by treatment with 80% aqueous acetic acid (HOAc) at 87° C. to give the title compound.

Scheme 5 illustrates a general method by which some of these compounds can be prepared, by illustrating the synthesis of [S-(R*,R*)]-2-(3-benzyl-3-methyl-ureido)-N-[2-(4-benzyloxy-phenyl)-1-(2-methyl-2-phenyl-propylcarbamoyl)-ethyl]-3-(1H-imidazol-4-yl)-N-methyl-propionamide (Example 5). Coupling of Boc-NMe-Tyr(OBn)-OH to β,β-dimethylphenethylamine hydrochloride was carried out in chloroform with benzotriazole-1-yl-oxy-tris-pyrrolidino-phosphonium hexafluorophosphate (PyBOP) as coupling agent, and triethylamine as the base. The resulting product was then treated with a saturated solution of HCl in diethyl ether to give H-NMe-Tyr(OBn)-NH-CH$_2$-C(CH$_3$)$_2$-phenyl.HCl(B).

H-His(Trt)-OCH$_3$ hydrochloride was reacted with 4-nitro-phenyl-chloroformate in the presence of triethylamine in methylene chloride, followed by the addition of benzylmethylamine. Saponification was then carried out with 1N NaOH in methanol:THF (1:1) followed by treatment with 1N HCl to give phenyl-CH$_2$-N(CH$_3$)-CO-His(Trt)-OH(A).

Products A and B were then coupled in chloroform with benzotriazole-1-yl-oxy-tris-pyrrolidino-phosphonium hexafluorophosphate (PyBOP) as coupling agent, and DIEA as the base. The resulting product was then treated with 80% aqueous acetic acid at 90° C. to give the title compound.

Scheme 6 illustrates a general method by which some of these compounds can be prepared, by illustrating the synthesis of [S-(R*,R*)]-[1-({[2-(4-benzyloxy-phenyl)-1-(1-phenyl-cyclobutylmethyl)-carbamoyl]-ethyl}-methyl-carbamoyl)-2-(3H-imidazol-4-yl)-ethyl]-carbamic acid benzyl ester (Example 6). Coupling of Boc-NMe-Tyr(OBn)-OH to C-(1-phenyl-cyclobutyl)-methylamine hydrochloride was carried out in methylene chloride with 2-(1H-benzotriazol-1-yl)-1,1,3,3-tetramethyluronium hexafluorophosphate (HBTU) as coupling agent, and DIEA as the base. The resulting product was treated with 20% trifluoroacetic acid (TFA) in methylene chloride. (S)-3-(4-Benzyloxy-phenyl)-2-methylamino-N-(1-phenyl-cyclobutylmethyl)-propionamide trifluoroacetate salt was then coupled in methylene chloride to Cbz-His(Trt)-OH with HBTU as coupling agent, and diisopropylethylamine (DIEA) as the base, followed by treatment with 50% TFA in methylene chloride to give the title compound.

Scheme 7 illustrates a general method by which some of these compounds can be prepared, by illustrating the synthesis of [S-(R*,R*)]-[2-(3H-imidazol-4-yl)-1-{methyl-[1-(2-methyl-2-phenyl-propylcarbamoyl)-2-phenyl-ethyl]-carbamoyl}-ethyl-carbamic acid benzyl ester (Example 7). Coupling of Boc-NMe-Phe-OH to β,β- dimethylphenethylamine hydrochloride was carried out in methylene chloride with dicyclohexylcarbodiimide (DCC) and 1-hydroxybenzotriazole (HOBt), as coupling agents, and DIEA as the base. The resulting product was treated with 30% trifluoroacetic acid (TFA) in methylene chloride. H-NMe-Phe-NH-CH$_2$-C(CH$_3$)$_2$-phenyl. TFA was then coupled in methylene chloride to Cbz-His(Trt)-OH with HATU and HOAt as coupling agents and diisopropylethylamine (DIEA) as the base, followed by treatment with 50% TFA in methylene chloride to give the title compound.

Scheme 8 illustrates a general method by which some of these compounds can be prepared by illustrating the synthesis of [S-(R*,R*)]-(2-(3H-imidazol-4-yl)-1-{methyl-[3-methyl-1-(2-methyl-2-phenyl-propylcarbamoyl)-butyl]-carbamoyl}-ethyl)-carbamic acid benzyl ester (Example 8). Coupling of Boc-NMe-Leu-OH to β,β-dimethylphenethylamine hydrochloride was carried out in methylene chloride:DMF (1:1) with HBTU as a coupling agent, and DIEA as the base. The resulting product was treated with 25% trifluoroacetic acid (TFA) in methylene chloride. H-NMe-Leu-NH-CH$_2$-C(CH$_3$)$_2$-phenyl.TFA was then coupled to methylene chloride:DMF (4:1) to Cbz-His(Trt)-OH, with HBTU as coupling agent, and diisopropylethylamine (DIEA) as the base, followed by treatment with 50% TFA in methylene chloride to give the title compound.

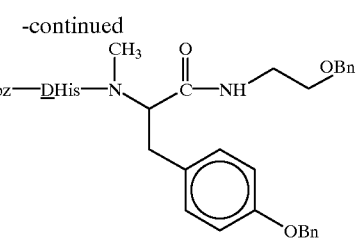

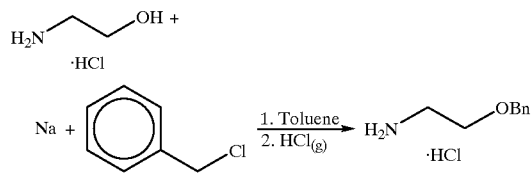

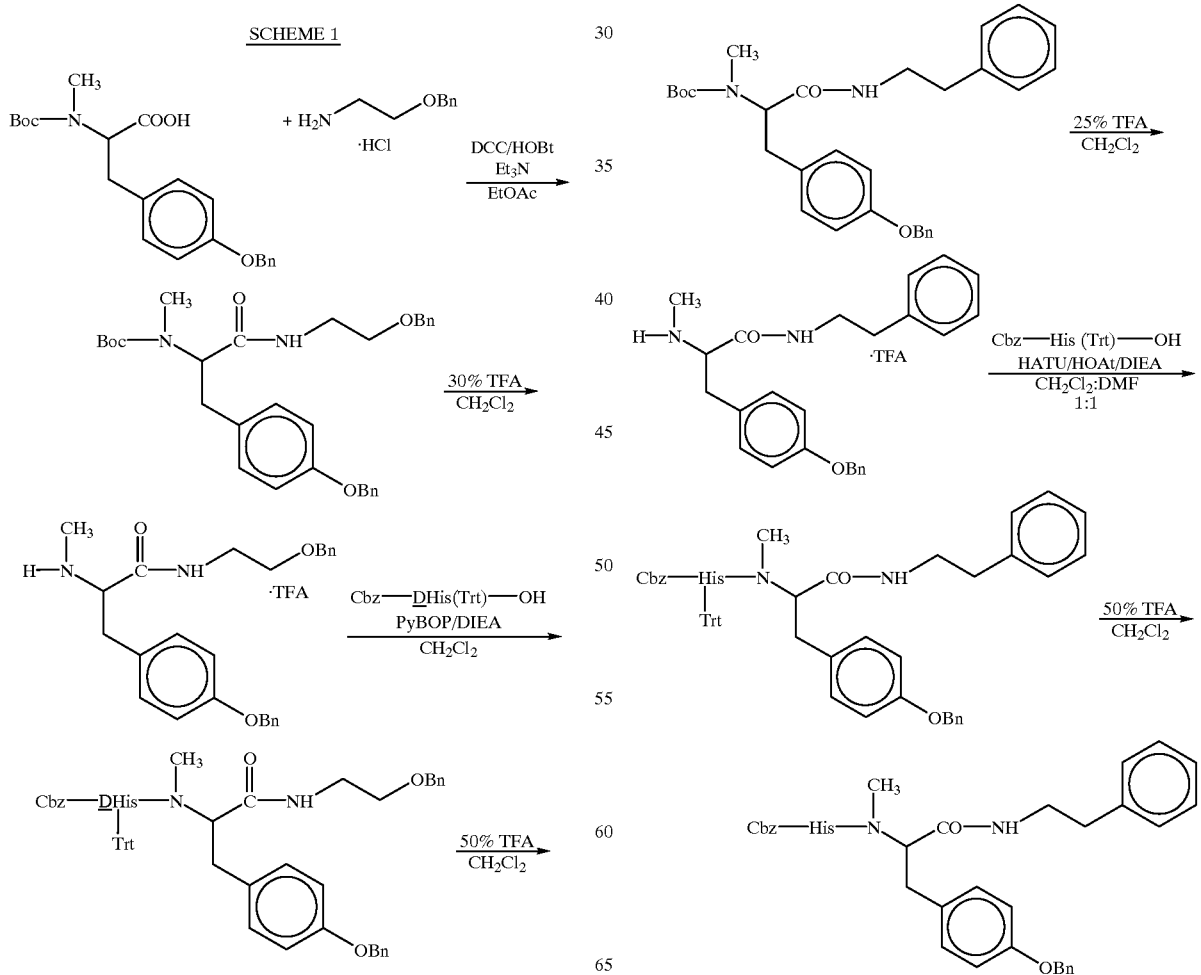

SCHEME 3
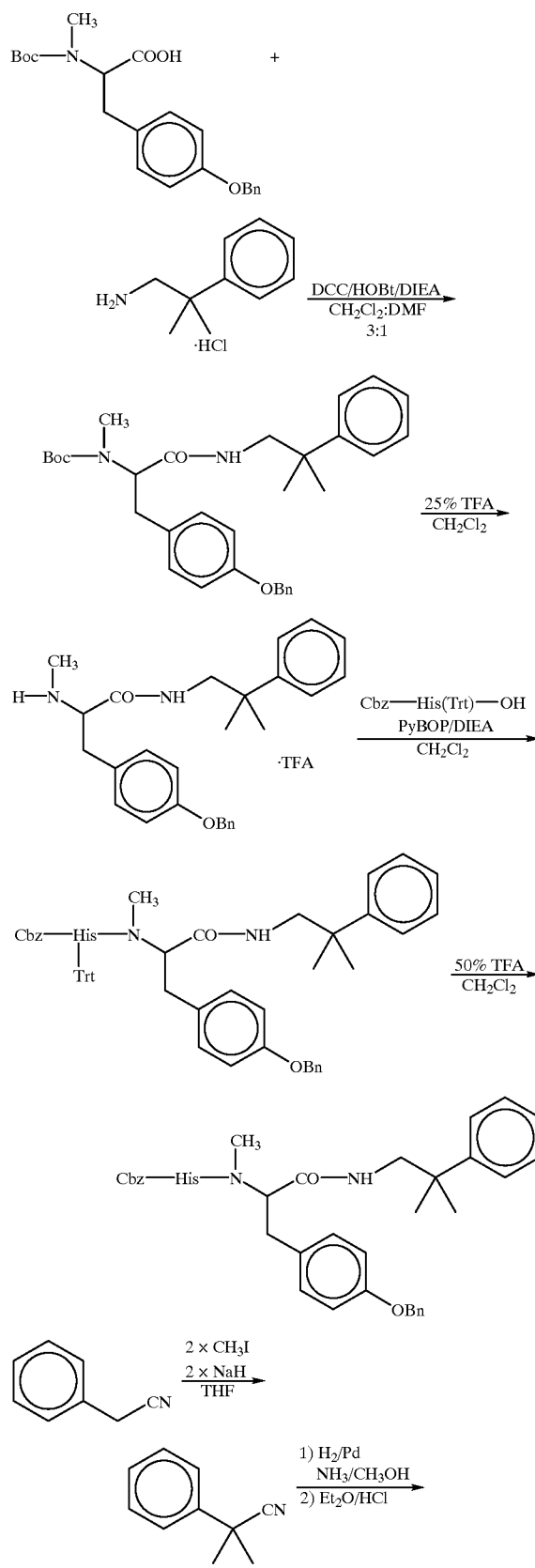
SCHEME 4
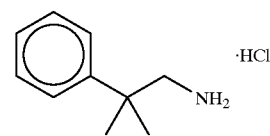
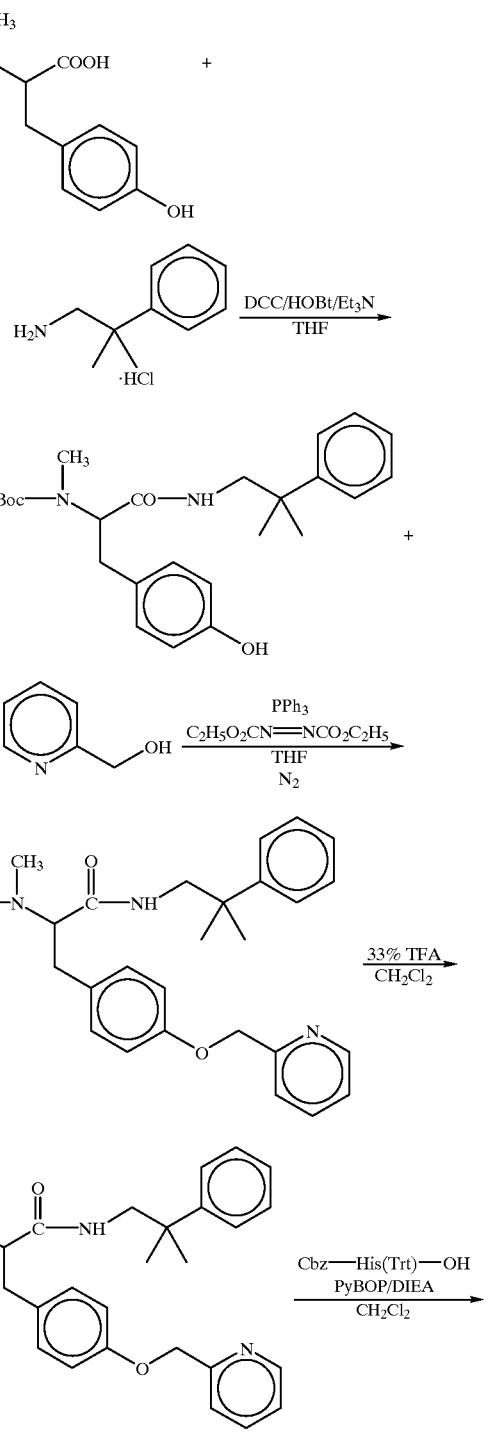

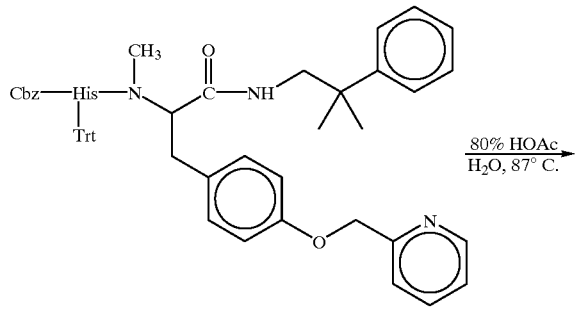
SCHEME 5
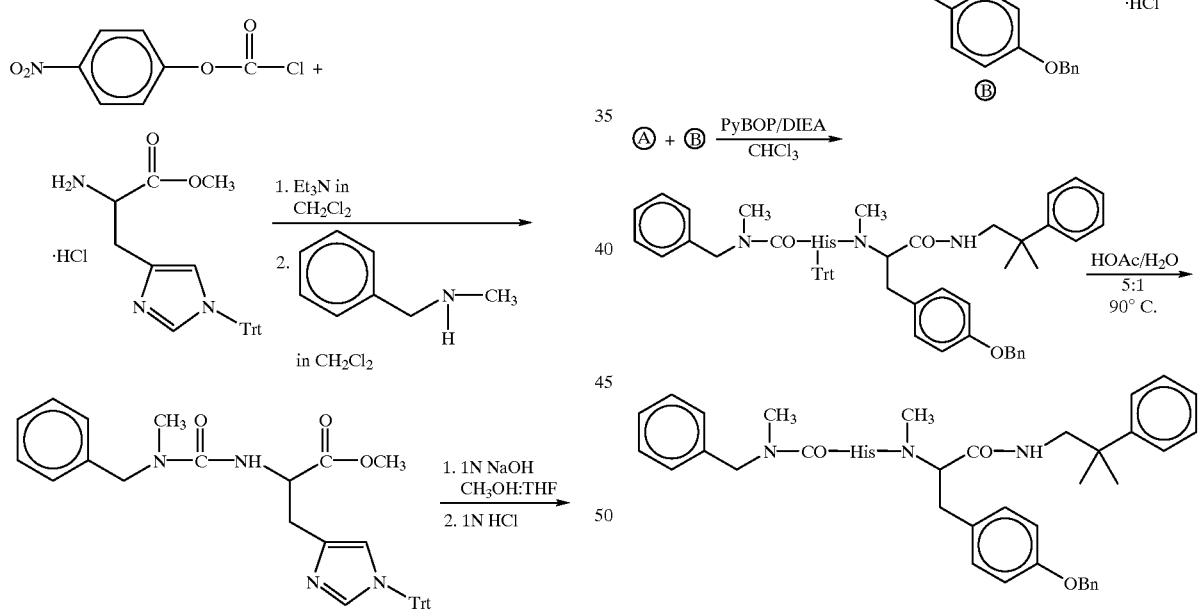
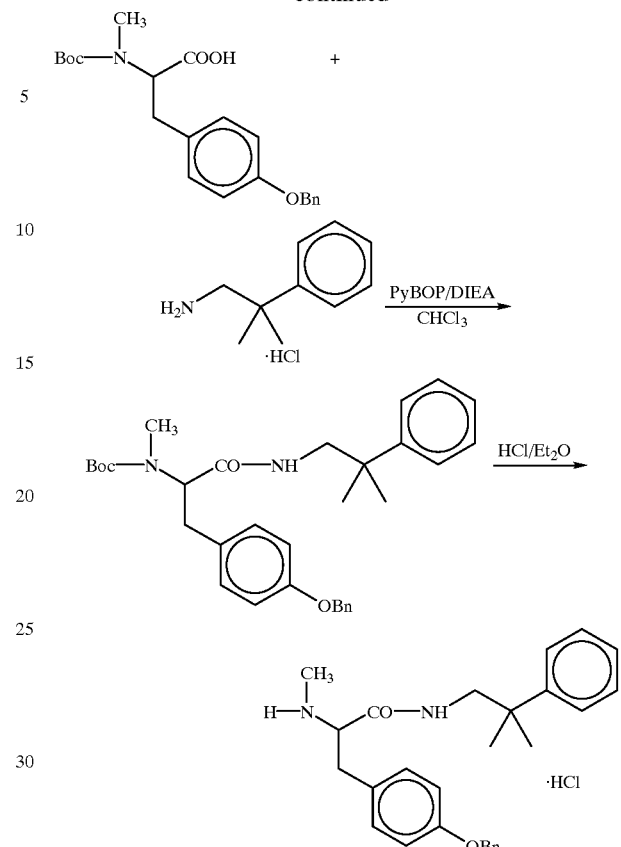
SCHEME 6
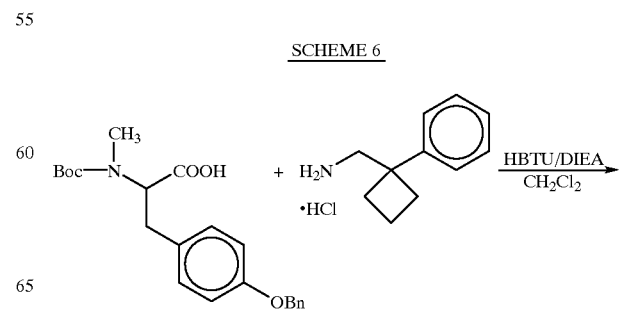

-continued
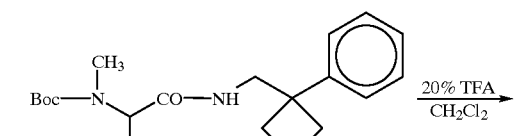
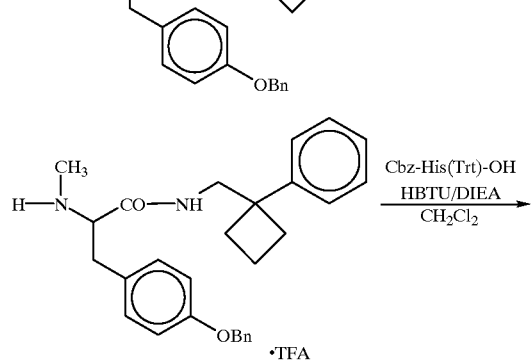
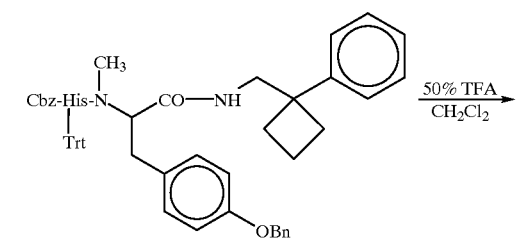
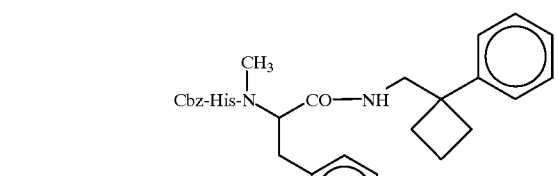
SCHEME 7
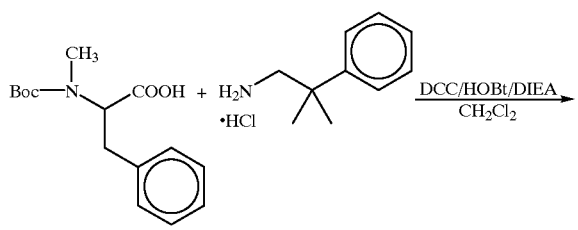
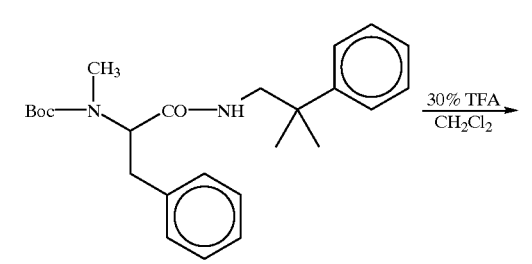
-continued
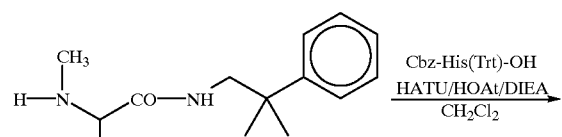
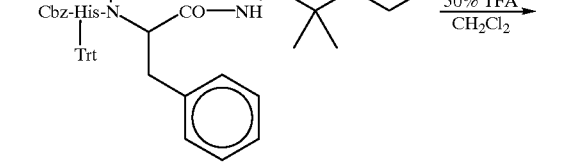
SCHEME 8
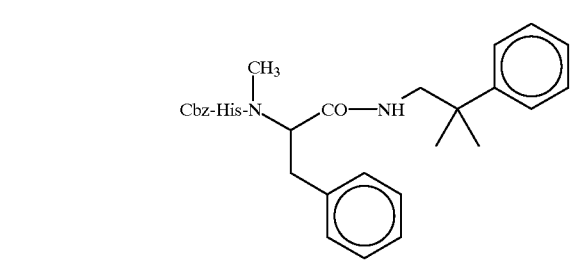
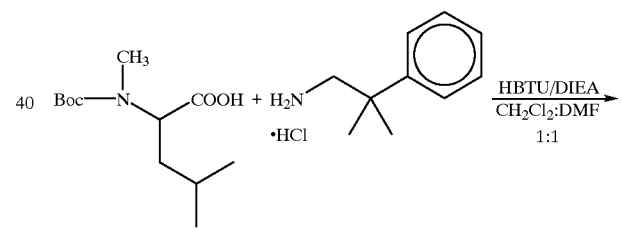
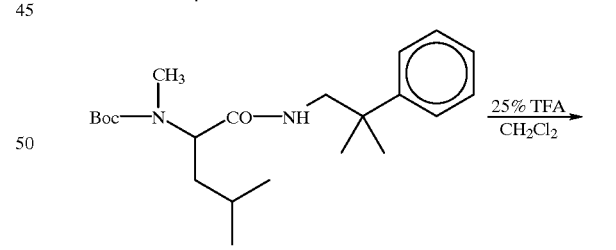

-continued

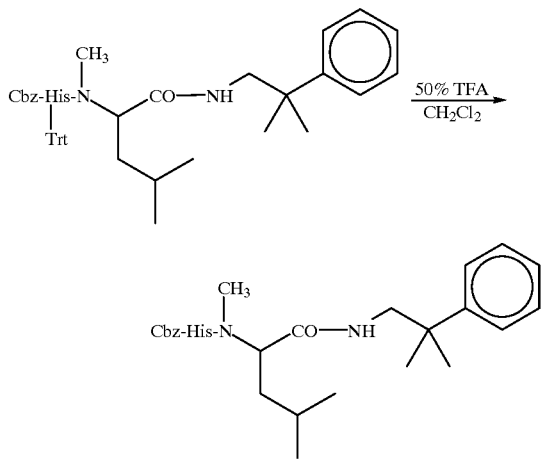

The following abbreviations are used herein:

| Abbreviations | |
|---|---|
| Cbz or Z | Carbobenzoxy |
| His | Histidine |
| Trt | Trityl |
| TEA | Triethylamine |
| HOAc | Acetic acid |
| $Et_2O$ | Diethylether |
| tBu | tert-Butyl |
| TFA | Trifluoroacetic acid |
| ES-MS | Electrospray Mass Spectrometry |
| FAB-MS | Fast Atom Bombardment Mass Spectrometry |
| HOBt | 1-Hydroxybenzotriazole |
| DCC | Dicyclohexylcarbodiimide |
| THF | Tetrahydrofuran |
| PyBOP | Benzotriazole-1-yl-oxy-tris-pyrrolidino-phosphonium hexafluorophosphate |
| DIEA | Diisopropylethylamine |
| DMF | Dimethylformamide |
| $Et_3N$ | Triethylamine |
| OAc | Acetate |
| $Et_2O$ | Diethyl ether |
| Boc | tert-Butoxycarbonyl |
| iBuOCOCl | Isobutylchloroformate |
| NMM | N-methylmorpholine |
| DMSO | Dimethylsulfoxide |
| HATU | (0-(7-Azabenzotriazol-1-yl)-1,1,3,3-tetramethyl uronium hexafluorophosphate |
| HOAt | 1-Hydroxy-7-azabenzotriazole |
| HBTU | 2-(1H-Benzotriazol-1-yl)-1,1,3,3-tetramethyl uronium hexafluorophosphate |
| EtOAc | Ethylacetate |
| $PPh_3$ | Triphenyl phosphine |
| Hepes | (N-[Z-hydroxyethyl]piperazine-N'-[2-ethanesulfonic acid]) |

EXAMPLE 1

[R-(R*,S*)]-[1-{[1-(2-Benzyloxy-ethylcarbamoyl)-2-(4-benzyloxy-phenyl)-ethyl]-methyl-carbamoyl}-2-(1H-imidazol-4-yl)-ethyl]-carbamic acid benzyl ester Step 1: Boc-NMe-Tyr(OBn)-NH-$CH_2CH_2$-OBn or (S)-[1-(2-Benzyloxy-ethylcarbamoyl)-2-(4-benzyloxy-phenyl)-ethyl]-methyl-carbamic acid tert-butyl ester To a solution of Boc-NMe-Tyr(OBn)-OH (0.82 g, 2.1 mmol) in ethyl acetate (100 mL) at 0° C. was added HOBt (0.40 g, 2.95 mmol) followed by DCC (0.53 g, 2.58 mmol) and 2-(phenylmethoxy)-ethylamine hydrochloride (from Step 5, below; 0.40 g, 2.1 mmol), followed by trimethylamine (0.31 mL, 2.2 mmol). The mixture was allowed to warm to room temperature and stirred overnight. The mixture was filtered, diluted with ethyl acetate, and washed twice with 2N HCl, 1N $NaHCO_3$, brine, dried over $MgSO_4$, filtered, and concentrated. The product was purified by flash chromatography (1:1 ethyl acetate:hexanes) (0.90 g, 1.7 mmol; 81%); MS-CI 519 (m+1).

Step 2: HNMe-Tyr(OBn)-NH-$CH_2$-$CH_2$-Obn.TFA or (S)-N-(2-Benzyloxy-ethyl-3-(4-benzyloxy-phenyl)-2-methylamino-propionamide.TFA Boc-NMe-Tyr(OBn)-NH-$CH_2$-$CH_2$-OBn (from Step 1, 0.90 g, 1.7 mmol) was treated with 50 mL of 30% trifluoroacetic acid (TFA) in methylene chloride. The solution was stirred at room temperature for 4 hours. The solution was concentrated, the residue taken up in methylene chloride and reconcentrated. This was repeated twice. The residue was dried in vacuo and used without further purification; MS-CI 419 (m+1).

Step 3: Cbz-DHis(Trt)-NMe-Tyr(OBn)-NH-$CH_2$-$CH_2$-OBn or [S-(R*,S*)]-[1-[1-(2-Benzyloxy-ethylcarbamoyl)-2-(4-benzyloxy-phenyl)-ethylcarbamoyl]-2-(1-trityl-1H-imidazol-4-yl)-ethyl]-carbamic acid benzyl ester To a solution of Cbz-DHis(Trt)-OH (synthesized according to the method in Hudspeth J. P., Kaltenbronn J. S., Repine J. T., Roark W. H., Stier M. A., Renin inhibitors III, U.S. Pat. No. 4,753,933; 1988) (0.94 g, 1.8 mmol) in methylene chloride (50 mL) was added benzotriazole-1-yloxy-tris-pyrrolidino-phosphonium hexafluorophosphate (PyBOP; 0.93 g, 1.8 mmol). HNMe-Tyr(OBn)-NH-$CH_2$-$CH_2$-OBn. TFA (from Step 2, 1.7 mmol) was added followed by diisopropylethylamine (DIEA; 0.76 mL, 4.4 mmol). The mixture was stirred overnight at room temperature. The solution was concentrated in vacuo, and the residue was taken up in ethyl acetate. The organic solution was washed twice with saturated $NaHCO_3$, brine, dried over $MgSO_4$, filtered, and concentrated (1.55 g, 1.66 mmol); MS-ES 933 (m+1).

Step 4: Cbz-DHis-NMe-Tyr(OBn)-NH-$CH_2$-$CH_2$-OBn or {R-(R*,S*)]-[1-{1-(2-Benzyloxy-ethylcarbamoyl)-2-(4-benzyloxy-phenyl)-ethyl-methyl-carbamoyl}-2-(1H-imidazol-4-yl)-ethyl]-carbamic acid benzyl ester Cbz-DHis(Trt)-NMe-Tyr(OBn)-NH-$CH_2$-$CH_2$-OBn (from Step 3, 1.55 g, 1.66 mmol) was treated with 50 mL of 50% TFA in methylene chloride. The solution was stirred at room temperature for 3 hours. The solution was concentrated, the residue taken up in methylene chloride, and reconcentrated. This was repeated twice. The residue was dried in vacuo. Purification was carried out on a portion of the product (0.2 g) by reverse-phase preparative HPLC (C-18 reverse-phase column, 20% to 65% of 0.1% TFA in acetonitrile against 0.1% TFA in water, 100 minutes, 13 mL/min) to give 18.5 mg of a white foam; MS-ES 690.3 (m+1). CHN: Calculated for $C_{40}H_{43}N_5O_6 \cdot 1.48CF_3COOH \cdot 0.49H_2O$ C, 59.46; H, 5.28; N, 8.07 Found: C, 59.46; H, 5.28; N, 8.12

Step 5: 2-(Phenylmethoxy)-ethylamine hydrochloride

Ethanolamine hydrochloride (20 g, 0.21 mol) in toluene (100 mL) was treated with sodium metal (pellets washed with hexane) (10.14 g, 0.44 mL). The reaction was refluxed until the sodium metal was no longer present. The mixture was cooled and benzyl chloride (24.17 mL, 0.21 mmol) was added, the reaction was stirred at room temperature overnight. The reaction mixture was filtered and the solid washed with toluene. The filtrate was cooled to 0° C. and HCl gas was bubbled in for 10 minutes. A white precipitate was obtained and filtered. The solid was recrystallized using 70 mL of isopropyl alcohol (10.4 g, 0.056 mol); MS-CI 188 (m+1).

EXAMPLE 2

[R-(R*,R*)]-[1-{[2-(4-Benzyloxy-phenyl)-1-phenethylcarbamoyl-ethyl]-methyl-carbamoyl}-2-(1H-imidazol-4-yl)-ethyl]-carbamic acid benzyl ester Step 1: Boc-NMe-Tyr(OBn)-NH-CH$_2$CH$_2$-phenyl or (S)-[2-(4-Benzyloxy-phenyl)-1-phenethylcarbamoyl-ethyl]-methyl-carbamic acid benzyl ester To a solution of Boc-NMe-Tyr(OBn)-NH-OH (0.77 g, 2.0 mmol) in methylene chloride:dimethylformamide (1:1; 20 mL) was added HOBt (0.30 g, 2.2 mmol) followed by 0.5 M DCC/CH$_2$Cl$_2$ (4.4 mL g, 2.2 mmol). After stirring 1 hour, phenethylamine (0.27 mL, 2.2 mmol) was added. The mixture was stirred overnight at room temperature. The mixture was filtered and the solvent removed in vacuo. The residue was taken up in ethyl acetate and washed twice saturated used without further purification.

Step 2: HNMe-Tyr(OBn)-NH—CH$_2$—CH$_2$-phenyl.TFA or (S)-3-(4-Benzyloxy-phenyl)-2-methylamino-N-phenethyl-propionamide.TFA Boc-NMe-Tyr(OBn)-NH—CH$_2$—CH$_2$-phenyl (from Step 1, 2.0 mmol) was treated with 50 mL of 25% trifluoroacetic acid (TFA) in methylene chloride. The solution was stirred at room temperature for 4 hours. The solvent was reduced in volume and cold diethyl ether was added to precipitate the product (0.87 g, 2 mmol); MS-CI 389 (m+1).

Step 3: Cbz-His(Trt)-NMe-Tyr(OBn)-NH—CH$_2$—CH$_2$-phenyl or [S-(R*,S*)]-[1-[1-(2-Benzyloxy-ethylcarbamoyl)-2-(4-benzyloxy-phenyl)-ethylcarbamoyl]-2-(1-trityl-1H-imidazol-4yl)-ethyl]-carbamic acid benzyl ester To a solution of Cbz-His(Trt)-OH (synthesized according to the method in Hudspeth J. P., Kaltenbronn J. S., Repine J. T., Roark W. H., Stier M. A., Renin inhibitors III, U.S. Pat. No. 4,735,933; 1988) (0.38 g, 0.7 mmol) in methylene chloride (5 mL) was added (O-(7-azabenzotriazol-1yl)-1,1,3,3-tetramethyl uronium hexafluorophosphate (HATU; 0.149 g, 0.4 mmol) and 1-hydroxy-7-azabenzotriazole (HOAt; 0.063 g, 0.5 mmol), dissolved in dimethylformamide (5 mL). HNMe-Tyr(OBn)-NH—CH$_2$—CH$_2$-phenyl.TFA (from Step 2, 0.25 g, 0.64 mmol) was added followed by diisopropylethylamine (DIEA; 0.275 mL, 1.6 mmol). The mixture was stirred overnight at room temperature. The solution was concentrated in vacuo, and the residue was taken up in ethyl acetate. The organic solution was washed twice with saturated NaHCO$_3$, brine, dried over MgSO$_4$, filtered, and concentrated to give 0.5 g of product (0.55 mmol), which was used without further purification.

Step 4: Cbz-His-NMe-Tyr(OBn)-NH—CH$_2$—CH$_2$-Phenyl or [S-(R*,R*)]-[1-{[2-(4-Benzyloxy-phenyl)-1-phenethylcarbamoyl-ethyl]-methyl-carbamoyl}-2-(1H-imidazol-4-yl)-ethyl]-carbamic acid benzyl ester Cbz-His(Trt)-NMe-Tyr(OBn)-NH—CH$_2$—CH$_2$-OBn (from Step 3, 0.5 g, 0.55 mmol) was treated with 50 mL of 50% TFA in methylene chloride. The solution was stirred at room temperature for 2 hours. The solvent was reduced in volume and diethyl ether/hexane (200 mL) was added to the residue. The solution was cooled to −40° C. overnight. The ether/hexane was decanted and the residue dried in vacuo. Purification was carried out by reverse-phase preparative HPLC (C-18) reverse-phase column, 20% to 60% of 0.1% TFA in acetonitrile against 0.1% TFA in water, 100 minutes, 13 mL/min) to give 37.5 mg of a white foam; MS-ES 661 (m+1).

CHN: Calculated for C$_{39}$H$_{42}$N$_5$O$_5$.1.37CF$_3$COOH.0.08H$_2$O C, 61.25; H, 5.36; N, 8.56 Found: C, 61.25; H, 5.36; N, 8.55

EXAMPLE 3

[S-(R*,R*)]-[1-{[2-(4-Benzyloxy-phenyl)-1-(2-methyl-2-phenyl-propylcarbamoyl)-ethyl]-methyl-carbamoyl}-2-(1H-imidazol-4-yl)-ethyl]-carbamic acid benzyl ester Step 1: Boc-NMe-Tyr(OBn)-NH—CH$_2$—C(CH$_3$)$_2$-phenyl or (S)-[2-(4-Benzyloxy-phenyl)-1-(2-methyl-2-phenyl-propylcarbamoyl)-ethyl]-methyl-carbamic acid tert-butyl ester To a solution of Boc-NMe-Tyr(OBn)-OH (1.54 g, 4.0 mmol) in methylene chloride:dimethylformamide (3:1; 20 mL) was added HOBt (0.60 g, 4.4 mmol) followed by 0.5 M DCC/CH$_2$Cl$_2$ (8.8 mL g, 4.4 mmol). β,β-Dimethyl-phenethylamine hydrochloride (from Step 5 below) (0.815 g, 4.4 mmol) and DIEA (0.80 mL, 4.6 mmol) were then added. The mixture was stirred overnight at room temperature. The mixture was filtered and the solvent removed in vacuo. The residue was taken up in ethyl acetate and washed twice saturated NaHCO$_3$, brine, dried over MgSO$_4$, filtered, and concentrated (1.81 g, 3.5 mmol; 87% yield); MS-APCI 518 (m+1).

Step 2: HNMe-Tyr(OBn)-NH—CH$_2$—C(CH$_3$)$_2$-phenyl.TFA or (S)-3-(4-Benzyloxy-phenyl)-2-methylamino-N-(2-methyl-2-phenyl-propyl)-proprionamide.TFA Boc-NMe-Tyr(OBn)-NH—CH$_2$—(CH$_3$)$_2$-phenyl (from Step 1, 3.5 mmol) was treated with 50 mL of 25% TFA in methylene chloride. The solution was stirred at room temperature for 2 hours. The solvent was reduced in volume and the residue was added to 1:1 hexanes/diethyl ether, which was stored overnight at −40° C. overnight to precipitate the product. The ether/hexane was decanted and the residue dried in vacuo (1.2 g, 2.8 mmol); MS-CI 389 (m+1). The product was used without further purification.

Step 3: Cbz-His(Trt)-NMe-Tyr(OBn)-NH—CH$_2$—C(CH$_3$)$_2$-phenyl or [S-(R*,R*)]-[1-{[2-(4-Benzyloxy-phenyl)-1-(2-methyl-2-phenyl-propylcarbamoyl)-ethyl]-methyl-carbamoyl}-2-(1-trityl-1H-imidazol-4-yl)-ethyl]-carbamic acid benzyl ester To a solution of Cbz-His(Trt)-OH (synthesized according to the method in Hudspeth J. P., Kaltenbronn J. S., Repine J. T., Roark W. H., Stier M. A., Renin inhibitors III, U.S. Pat. No. 4,735,933; 1988) (0.64 g, 1.2 mmol) in methylene chloride (5 mL) was added benzotriazole-1-yl-oxy-tris-pyrrolidino-phosphonium hexafluorophosphate (PyBOP; 0.62 g, 1.2 mmol). HNMe-Tyr(OBn)-NH—CH$_2$—C(CH$_3$)$_2$-phenyl.TFA (from Step 2, 0.58 g, 1.2 mmol) was added followed by diisopropylethylamine (DIEA; 0.545 mL, 3.3 mmol). The mixture was stirred overnight at room temperature. The solution was concentrated in vacuo, and the residue was taken up in ethyl acetate. The organic solution was washed twice with saturated NaHCO$_3$, brine, dried over MgSO$_4$, filtered, and concentrated. The product was used without further purification.

Step 4: Cbz-His-NMe-Tyr(OBn)-NH—CH$_2$-C(CH$_3$)$_2$-phenyl or [S-(R*,R*)]-[1-{[2-(4-Benzyloxy-phenyl)-1-(2-methyl-2-phenyl-propylcarbamoyl)-ethyl]-methyl-carbamoyl}-2-(1H-imidazol-4-yl)-ethyl]-carbamic acid benzyl ester Cbz-His(Trt)-NMe-Tyr(OBn)-NH—CH$_2$-C(CH$_3$)$_2$-phenyl (from Step 3, 1.2 mmol) was treated with 50 mL of 50% TFA in methylene chloride. The solution was stirred at room temperature for 2 hours. The solvent was reduced in volume and the residue was added to 1:1 hexanes:diethyl ether, which was stored overnight at −40° C. overnight to precipitate the product. The ether/hexane was decanted and the residue dried to vacuo. Purification was carried out by reverse-phase preparative HPLC (C-18) reverse-phase column, 20% to 60% of 0.1% TFA in acetonitrile against 0.1% TFA in water, 100 minutes, 13 mL/min) to give 25 mg of a white foam (4%); MS-ES 688 (m+1).

CHN: Calculated for $C_{41}H_{45}N_5O_5 \cdot 1.11CF_3COOH \cdot 1.67H_2O$ C, 61.44; H, 5.90; N, 8.29 Found: C, 61.44; H, 5.90; N, 8.11

Step 5: β,β-Dimethylphenethylamine hydrochloride

Sodium hydride (60% in oil) (17 g, 0.43 mol) was suspended in THF (150 mL) and cooled to 0° C. under nitrogen. Benzyl cyanide (22.2 g, 0.19 mol) in THF (30 mL) was added dropwise and the reaction was left to stir for 1 hour. Iodomethane (24.9 mL, 0.4 mmol) in THF (20 mL) was added dropwise at 0° C. The reaction was stirred at room temperature overnight, under nitrogen. The solution was filtered, and the filtrate removed in vacuo. The residue was taken up in ethyl acetate (100 mL) and washed 3 times with 10% $NaHSO_3$, saturated $NaHCO_3$, brine, dried over $MgSO_4$, and concentrated; 22.74 g (92%).

Reduction of the above product was carried out in the presence of Raney nickel, in methanol/$NH_3$. The catalyst was removed and washed with methanol. The filtrate was concentrated and diethyl ether (100 mL) and added to the residue. Concentrated HCl was added dropwise to precipitate the desired product; 24.8 g (86%).

EXAMPLE 4

[S-(R*,R*)]-[2-(1H-Imidazol-4-yl)-1-(methyl-{1-(2-methyl-2-phenyl-propylcarbamoyl)-2-[4-(pyridin-2-ylmethoxy)-phenyl]-ethyl}-carbamoyl)-ethyl]-carbamic acid benzyl ester Step 1: Boc-NMe-Tyr-NH—$CH_2$—$C(CH_3)_2$-phenyl A solution of Boc-NMe-Tyr-OH (3.87 g, 13.1 mmol) in tetrahydrofuran (THF) (70 mL) was treated with β,β-dimethylphenethylamine hydrochloride (from Step 5, Example 3) (2.44 g, 13.1 mmol), HOBt (1.78 g, 13.1 mmol) and DCC (2.74 g, 13.1 mmol). Triethylamine (1.9 mL, 13.1 mmol) was then added and the mixture stirred at room temperature for 2 days. A solution of 1N citric acid (26 mL, 26 mmol) was then added and the mixture filtered. The filtrate was diluted with ethyl acetate and washed with 1N citric acid, water, and brine. It was dried over $MgSO_4$ and removal of the solvent under reduced pressure gave the crude product (6.85 g). On adding chloroform/ethyl acetate, the HOBt precipitated and it was removed by filtration. The solvent was removed under reduced pressure and the residue chromatographed ($CHCl_3$:$CH_3OH$ 98:2) to give the product (4.32 g, 8.4 mmol; 77% yield); MS-APCI 427 (m+1).

Step 2: Boc-Nme-Tyr-(O—$CH_2$)-(2-pyridyl))-NH—$CH_2$—$C(CH_3)_2$-phenyl or (S)-Methyl-{1-(2-methyl-2-phenyl-propylcarbamoyl)-2-[4-(pyridin-2-ylmethoxy)-phenyl]-ethyl}-carbamic acid tert-butyl ester Under nitrogen atmosphere, a solution of Boc-NMe-Tyr-NH—$CH_2$—$C(CH_3)_2$-phenyl (from Step 1) (4.32 g, 10.1 mmol) in THF (50 mL) was treated with 2-pyridylcarbinol (1.1 mL, 11.1 mmol) and triphenylphosphine (2.69 g, 10.1 mmol). The solution was cooled in ice and treated dropwise over 20 minutes, with diethyl azodicarboxylate (1.6 mL, 10.1 mmol) in THF (5 mL). The cooling was removed and the solution allowed to stir at room temperature for 3 days. The solution was diluted with ethyl acetate and washed 3 times with water, brine, dried over $MgSO_4$ and the solvent removed in vacuo (10.8 g). The residue was chromatographed ($CHCl_3$:$CH_3OH$ 98:2) to give the product (4.38 g, 8.4 mmol; 84% yield); MS-APCI 518 (m+1).

Step 3: HNMe-Tyr(O—$CH_2$-(2-pyridyl))-NH—$CH_2$—$C(CH_3)_2$-phenyl or (S)-2-Methylamino-N-(2-methyl-2-phenyl-propyl)-3-[4-(pyridin-2-ylmethoxy)-phenyl]-propionamide.TFA A solution of Boc-NMe-Tyr(O—$CH_2$-(2-pyridyl))-NH—$CH_2$—$C(CH_3)_2$-phenyl (from Step 2, 1.8 g, 3.5 mmol) in methylene chloride (20 mL) was treated with trifluoroacetic acid (10 mL) and allowed to stir at room temperature for 1 hour. The solvent was removed under reduced pressure and then the residue was taken up in ethyl acetate. This solution was washed twice with saturated $NaHCO_3$, brine, dried over $MgSO_4$, and the solvent removed under reduced pressure to give the product (1.39 g, 3.3 mmol); MS-APCI 418 (m+1).

Step 4: Cbz-His(Trt)-NMe-Tyr(O—$CH_2$-(2-pyridyl))-NH—$CH_2$—$C(CH_3)_2$-phenyl or [S-(R*,R*)]-[1-(Methyl-{1-(2-methyl-2-phenyl-propylcarbamoyl)-2-[4-(pyridin-2-ylmethoxy)-phenyl]-ethyl}-carbamoyl)-2-(1-trityl-1H-imidazol-4-yl)-ethyl]-carbamic acid benzyl ester A solution of HNMe-Tyr(O $CH_2$-(2-pyridyl))-NH—$CH_2$—$C(CH_3)_2$-phenyl (from Step 3) (1.39 g, 3.3 mmol) in methylene chloride (50 mL) was treated with Cbz-His-(Trt)-OH (synthesized according to the method in Hudspeth J. P., Kaltenbronn J. S., Repine J. T., Roark W. H., Stier M. A., Renin inhibitors III, U.S. Pat. No. 4,735,933; 1988) (1.78 g, 3.3 mmol). The solution was cooled in ice and treated with DIEA (1.8 mL, 9.9 mmol), followed by PyBOP (1.75 g, 3.3 mmol). The cooling was removed and the solution stirred at room temperature for 2 days. The solvent was removed in vacuo and the residue taken up in ethyl acetate, and washed twice with water and brine. Drying over $MgSO_4$ and removal of the solvent under reduced pressure gave the crude product. It was taken up in a small amount of ethyl acetate, and filtered. Removal of the solvent under reduced pressure gave 3.39 g of the crude product. Chromatography ($CHCl_3$:$CH_3OH$ 98:2) gave the desired product (2.01 g, 2.2 mmol; 65% yield); MS-ES 932 (m+1).

Step 5: Cbz-His-NMe-Tyr(O—$CH_2$-(2-pyridyl))-NH—$CH_2$-$C(CH_3)_2$-phenyl or [S-(R*,R*)]-[2-(1H-Imidazol-4-yl)-1-(methyl-{1-(2-methyl-2-phenyl-propylcarbamoyl)-2-[4-(pyridin-2-ylmethoxy)-phenyl]-ethyl}-carbamoyl)-ethyl]-carbamic acid benzyl ester A solution of Cbz-His(Trt)-NMe-Tyr(O—$CH_2$-(2-pyridyl))-NH—$CH_2$—$C(CH_3)_2$-phenyl (from Step 4, 1.49 g, 1.6 mmol) in 80% acetic acid/water (100 mL) was heated at 87° C. for 30 minutes. The solvent was removed under reduced pressure and the residue taken up in ethyl acetate, and washed twice with saturated $NaHCO_3$ and brine. Drying over $MgSO_4$ and removal of the solvent under reduced pressure gave the crude product. Chromatography ($CHCl_3$:$CH_3OH$ 95:5) gave the product. It was dissolved in methylene chloride and the solvent removed under reduced pressure to give the desired product (0.82 g, 1.2 mmol; 74% yield); MS-APCI 690 (m+1).

CHN: Calculated for $C_{40}H_{44}N_6O_5 \cdot 0.2CH_2Cl_2$ C, 68.41; H, 6.34; N, 11.91 Found: C, 68.59; H, 6.32; N, 11.87

EXAMPLE 5

[S-(R*,R*)]-2-(3-Benzyl-3-methyl-ureido)-N-[2-(4-benzyloxy-phenyl)-1-(2-methyl-2-phenyl-propyl-carbamoyl)-ethyl]-3-(1H-imidazol-4-yl)-N-methyl-propionamide Step 1: Phenyl-$CH_2$—$N(CH_3)$—CO-His(Trt)-$OCH_3$ or (S)-2-(3-Benzyl-3-methyl-ureido)-3-(1-trityl-1H-imidazol-4-yl)-propionic acid methyl ester Histidine-(trityl)-methyl ester hydrochloride (20 g, 0.042 mol) was suspended in methylene chloride (300 mL) and washed twice with saturated $NaHCO_3$, brine, dried over $MgSO_4$, filtered, and cooled to 0° C. Triethylamine (6.54 mL, 0.047 mol) and 4-nitro-phenyl-chloroformate (9.38 g, 0.047 mol) were added and the solution stirred for 1 hour. Benzylmethylamine (11.4 mL, 0.088 mol) in methylene chloride (100 mL) was then added dropwise. The reaction was stirred at room temperature for 72 hours. The solvent was removed in vacuo. Ethyl acetate was added to the residue, and it was washed 3 times with saturated $NaHCO_3$, water, and brine. The solution was dried over $MgSO_4$, filtered, and concentrated in vacuo. The oil was chromatographed ($CHCl_3$ to $CHCl_3$:$CH_3OH$ 96:4) to give the desired product (11.55 g, 0.021 mol; 49% yield); MS-APCI 559 (m+1).

Step 2: Phenyl-$CH_2$—N($CH_3$)—CO-His(Trt)-OH or (S)-2-(3-Benzyl-3-methyl-ureido)-3-(1-trityl-1H-imidazol-4-yl)-propionic acid Phenyl-$CH_2$—N($CH_3$)—CO-His(Trt)-$OCH_3$ (from Step 1; 6.66 g, 0.012 mol) was dissolved in $CH_3OH$:THF (50 mL each). 1N NaOH (36 mL, 0.036 mol) was added dropwise and the solution was stirred at room temperature for 1.5 hours. The solvent was removed in vacuo. 1N HCl (36 mL, 0.036 mol) was added to the residue. The product was extracted with ethyl acetate. The organic solution was then washed with brine, dried over $MgSO_4$, filtered, and concentrated in vacuo. The solid product crystallized (5.83 g, 0.011 mol; 89% yield); MS-APCI 545 (m+1).

Step 3: Boc-NMe-Tyr(OBn)-NH—$CH_2$—C($CH_3$)$_2$-phenyl or (S)-[2-(4-Benzyloxy-phenyl)-1-(2-methyl-2-phenyl-propylcarbamoyl)-ethyl]-methyl-carbamic acid tert-butyl ester Boc-NMe-Tyr(OBn)-OH (0.83 g, 2.1 mmol), β,β-dimethylphenethylamine hydrochloride (from Step 5, Example 3) (0.44 g, 2.4 mmol), and DIEA (0.84 mL, 4.8 mmol) were dissolved in chloroform (20 mL) and cooled at 0° C., under nitrogen. After 15 minutes, PyBOP (1.25 g, 2.4 mmol) was added and the reaction was stirred at room temperature for 48 hours. The solvent was removed in vacuo and ethyl acetate was added to the residue. The organic solution was washed twice with water, saturated $NaHCO_3$, brine, dried over $MgSO_4$, filtered, and concentration in vacuo. The oil obtained was purified by chromatography (ethyl acetate:hexane 70:30) (1.08 g, 2.1 mmol; 100% yield); MS-APCI 517 (m+1).

Step 4: H NMe-Tyr(OBn)-NH—$CH_2$—C($CH_3$)$_2$-phenyl or (S)-3-(4-Benzyloxy-phenyl)-2-methylamino-N-(2-methyl-2-methyl-2-phenyl-propyl)-propionamide.TFA Boc-NMe-Tyr(OBn)-NH—$CH_2$-C($CH_3$)$_2$-phenyl (from Step 3, 1.04 g, 2 mmol) was dissolved in diethyl ether saturated with HCl. The reaction was stirred overnight at room temperature. The solvent was removed in vacuo to give the product which was used without further purification. (1.0 g, 2.4 mmol); MS-APCI 417 (m+1).

Step 5: Phenyl-$CH_2$—N($CH_3$)—CO-His(Trt)-NMe-Tyr(OBn)-NH—$CH_2$—C($CH_3$)$_2$-phenyl or [S-(R*,R*)]-2-(3-Benzyl-3-methyl-ureido)-N-[2-(4-benzyloxy-phenyl)-1-(2-methyl-2-phenyl-propylcarbamoyl)-ethyl]-N-methyl-3-(1-trityl-1H-imidazol-4-yl)-propionamide Phenyl-$CH_2$—N($CH_3$)—CO-His(Trt)-OH (from Step 2, 1.09 g, 2.0 mmol), H-NMe-Tyr(OBn)-NH—$CH_2$—C($CH_3$)$_2$-phenyl (from Step 4; 0.80 g, 1.8 mmol) and DIEA (0.71 mL, 4.1 mmol) were dissolved in chloroform (20 mL) and cooled to 0° C., under nitrogen. After 15 minutes, PyBOP (1.04 g, 2.0 mmol) was added and the reaction was stirred at room temperature overnight. The solvent was removed in vacuo and ethyl acetate was added to the residue. The organic solution was washed twice with water, saturated $NaHCO_3$, brine, dried over $MgSO_4$, filtered, and concentrated in vacuo. The residue obtained was purified by chromatography (ethyl acetate:hexane 70:30) (1.39 g, 1.5 mmol; 85% yield); MS-APCI 943 (m+1).

Step 6: Phenyl-$CH_2$—N($CH_3$)—CO-His-NMe-Tyr(OBn)-NH—$CH_2$—C($CH_3$)$_2$-phenyl or [S-(R*,R*)]-2-(3-Benzyl-3-methyl-ureido)-N-[2-(4-benzyloxy-phenyl)-1-(2-methyl-2-phenyl-propylcarbamoyl)-ethyl]-3-(1H-imidazol-4-yl)-N-methyl-propionamide Phenyl-$CH_2$—N($CH_3$)—CO-His-NMe-Tyr(OBn)-NH—$CH_2$—C($CH_3$)$_2$-phenyl (from Step 5; 1.39 g, 1.5 mmol) was dissolved in acetic acid:water (5:1, 12 mL) and heated to 90° C. for 30 minutes. The solvent was removed in vacuo. Ethyl acetate was added to the residue and washed twice with saturated $NaHCO_3$, brine, dried over $MgSO_4$, filtered, and concentrated in vacuo. The oil obtained was chromatographed ($CHCl_3$ to $CHCl_3$:$CH_3OH$ 94:6) (0.34 g 0.5 mmol; 32% yield); MS-APCI 701 (m+1).

CHN: calculated for $C_{42}H_{48}N_6O_4 \cdot 0.27 CHCl_3 \cdot 0.32 H_2O$ C, 68.71; H, 6.67; N, 11.37 Found: C, 68.71; H, 6.71; N, 11.23

EXAMPLE 6

[S-(R*,R*)]-[1-{[2-(4-Benzyloxy-phenyl)-1-[(1-phenyl-cyclobutylmethyl)-carbamoyl]-ethyl}-methyl-carbamoyl)-2-(3H-imidazol-4-yl)-ethyl]-carbamic acid benzyl ester Step 1: (S)-{2-(4-Benzyloxy-phenyl)-1-[(1-phenyl-cyclobutylmethyl)-carbamoyl]-ethyl}-methyl-carbamic acid tert-butyl ester A suspension of Boc-NMe-Tyr(OBn)-OH (0.90 g, 2.3 mmol) and C-(1-phenyl-cyclobutyl)-methylamine hydrochloride (synthesized according to the method in Bridges, A. J., Hamilton, H. W., Moos, W. H., Szotek, D. L., $N^6$-substituted Adenosines, U.S. Pat. No. 4,755,594) (0.46 g, 2.3 mmol) and 2-(1H-benzotriazole-1-yl)-1,1,3,3-tetramethyluronium hexafluorophosphate (HBTU) (0.97 g, 5.6 mmol) in methylene chloride (10 mL) was treated with DIEA (0.86 mL, 5.1 mmol). The suspension was stirred at room temperature overnight. The resulting solution was concentrated. The residue was taken up in ethyl acetate. The solution was washed with 0.5 M HCl, saturated $NaHCO_3$, dried over $MgSO_4$, filtered, and concentrated. The oil was chromatographed ($CH_2Cl_2$:$CH_3OH$ 50:1) to give the desired product (1.07 g, 2.02 mmol; 87% yield). MS-APCI 529 (m+1).

Step 2: (S)-3-(4-Benzyloxy-phenyl)-2-methylamino-N-(1-phenyl-cyclobutylmethyl)-propionamide trifluoroacetate salt To a solution of (S)-{2-(4-Benzyloxy-phenyl)-1-[(1-phenyl-cyclobutylmethyl)-carbamoyl]-ethyl}-methyl-carbamic acid tert-butyl ester (from Step 1; 1.07 g, 2.02 mmol) in methylene chloride (10 mL) was added TFA (2.5 mL). The solution was stirred at room temperature for 2 hours and then concentrated in vacuo. Coevaporisation with methylene chloride was carried out twice to give the desired product which was used without further purification.

Step 3: [S-[R*,R*)]-[1-({2-(4-Benzyloxy-phenyl)-1-[(1-phenyl-cyclobuty-methyl)-carbamoyl}-ethyl}-methyl-carbamoyl)-2-(1-trityl-1H-imidazol-4-yl)-ethyl}-carbamic acid benzyl ester To a suspension of Cbz-His-(Trt)-OH (synthesized according to the method in Hudspeth J. P., Kaltenbronn J. S., Repine J. T., Roark W. H., Stier M. A., Renin inhibitors III, U.S. Pat. No. 4,735,933; 1988) (1.24 g, 2.33 mmol), (S)-3-(4-Benzyloxy-phenyl)-2-methylamino-N-(1-phenyl-cyclobutylmethyl)-propionamide trifluoroacetate salt (from Step 2, 2.02 mmol) and HBTU (0.97 g, 2.56 mmol) in methylene chloride (20 mL), at 0° C., was added DIEA (0.86 mL, 6.99 mmol). The reaction was warmed to room temperature and stirred overnight. The solution was concentrated. The residue was taken up in ethyl acetate. The solution was washed with 0.5 M HCl, saturated NaHCO$_3$, dried over MgSO$_4$, filtered, and concentrated. The oil was chromatographed (CH$_2$Cl$_2$:CH$_3$OH 15:1) to give the desired product (1.28 g, 1.36 mmol; 58% yield for Steps 2 and 3); MS-APCI 942 (m+1).

Step 4: [S-[R*,R*)]-[1-({2-(4-Benzyloxy-phenyl)-1-[(1-phenyl-cyclobutylmethyl)-carbamoyl}-ethyl}-methyl-carbamoyl)-2-(3H-imidazol-4-yl)-ethyl}-carbamic acid benzyl ester To a solution of [S-[R*,R*)]-[1-({2-(4-Benzyloxy-phenyl)-1-[(1-phenyl-cyclobutymethyl)-carbamoyl}-ethyl}-methyl-carbamoyl)-2-(1-trityl-1H-imidazol-4-yl)-ethyl]-carbamic acid benzyl ester (from Step 3, 1.28 g, 1.36 mmol) in methylene chloride (10 mL) was added TFA (10 mL). The solution was stirred at room temperature for 2 hours and concentrated. The residue was dissolved in ethyl acetate and the solution was washed with saturated NaHCO$_3$, dried over MgSO$_4$, filtered, and concentrated. The residue was purified twice by chromatography (first: CH$_2$Cl$_2$:CH$_3$OH 10:1; second: CH$_2$Cl$_2$:CH$_3$OH 15:1) (0.23 g, 0.33 mmol; 24% yield); MS-APCI 700 (m+1).

CHN: Calculated for C$_{42}$H$_{45}$N$_5$O$_5$.0.25H$_2$O C, 71.62; H, 6.51; N, 9.94 Found: C, 71.62; H, 6.51; N, 9.91

EXAMPLE 7

[S-R*,R*)]-(2-(3H-Imidazol-4-yl)-1-{methyl-[1-2-methyl-2-phenyl-propyl-carbamoyl)-2-phenyl-ethyl]-carbamoyl}-ethyl)-carbamic Acid Benzyl Ester Step 1: Boc-NMe-Phe-NH-CH$_2$-C(CH$_3$)$_2$-phenyl or (S)-Methyl-[1-(2-methyl-2-phenyl- propylcarbamoyl)-2-phenyl-ethyl]-carbamic Acid Tert-butyl Ester Boc-NMe-Phe-OH (0.28 g, 1.0 mmol) was dissolved in methylene chloride (50 mL). N-hydroxybenzotriazole (HOBt) (0.17 g, 1.2 mmol) was added followed by 0.5M DCC/CH$_2$Cl$_2$ (2.4 mL, 1.25 mmol), β,β-dimethylphenethylamine hydrochloride (from Step 5, Example 3) (0.20 g, 1.1 mmol) and DIEA (0.39 mL, 2.2 mmol). The reaction was stirred at room temperature under nitrogen for 48 hours. The solution was filtered and concentrated in vacuo. The residue was taken up in ethyl acetate and washed twice with 2N HCl, 1N NaHCO$_3$, brine, dried over MgSO$_4$, filtered, and concentrated. The residue was chromatographed (CHCl$_3$:CH$_3$OH 95:5) (0.32 g, 0.78 mmol, 78%). NMR confirmed the structure of the product.

Step 2: HNMe-Phe-NH-CH$_2$-C(CH$_3$)$_2$-phenyl trifluoroacetate or (S)-2-Methylamino-N-(2-methyl-2-phenyl-propyl)-3-phenyl-propionamide.TFA Boc-NMe-Phe-NH-CH$_2$-C(CH$_3$)$_2$-phenyl (from Step 1, 0.32 g, 0.78 mmol) was treated with 30% TFA/CH$_2$Cl$_2$ (50 mL) for 2 hours at room temperature. The solution was concentrated. Coevaporisation with methylene chloride was carried out twice to give the desired product which was used without further purification. NMR confirmed the structure of the product.

Step 3: Cbz-His(Trt)-NMe-Phe-NH-CH$_2$-C(CH$_3$)$_2$-phenyl or [S-(R*,R*)]-[1- {Methyl-[1-(2-methyl-2-phenyl-propylcarbamoyl)-2-phenyl-ethyl]- carbamoyl}-2-(1-trityl-1H-imidazol-4-yl)-ethyl]-carbamic Acid Benzyl Ester HNMe-Phe-NH-CH$_2$-C(CH$_3$)$_2$-phenyl trifluoroacetate (from Step 2; 0.78 mmol) was dissolved in methylene chloride (40 mL). Cbz-His-(Trt)-OH (synthesized according to the method in Hudspeth J. P., Kaltenbronn J. S., Repine J. T., Roark W. H., Stier M. A., Renin inhibitors III, U.S. Pat. No. 4,735,933; 1988) (0.46 g, 0.87 mmol) was added followed by HOAt (0.23 g, 1.7 mmol), HATU (0.60 g, 1.6 mmol), and DIEA (0.95 mL, 5.5 mmol). The reaction was stirred at room temperature under nitrogen for 48 hours. The solution was concentrated in vacuo. The residue was taken up in ethyl acetate and washed twice with 5% citric acid, 5% NaHCO$_3$, brine, dried over MgSO$_4$, filtered, and concentrated. The product was used without further purification. NMR confirmed the structure of the product.

Step 4: [S-(R*,R*)]-(2-(3H-Imidazol-4-yl)-1-{methyl-[1-(2-methyl-2-phenyl- propylcarbamoyl)-2-phenyl-ethyl]-carbamoyl}-ethyl)-carbamic Acid Benzyl Ester Cbz-His(Trt)-NMe-Phe-NH-CH$_2$-C(CH$_3$)$_2$-phenyl (from Step 3, 0.78 mmol) was treated with 50% TFA/CH$_2$Cl$_2$ (50 mL) for 2 hours at room temperature. The solution was concentrated. Coevaporisation with methylene chloride was carried out twice to give the crude product. Purification was carried out by reverse-phase preparative HPLC (C-18 reverse-phase column, 20% to 60% of 0.1% TFA in acetonitrile against 0.1% TFA in water, 100 minutes, 13 mL/min) to give the desired product (0.0458 g, 10%); MS-APCI 582 (m+1). Proton NMR confirmed the structure.

CHN: Calculated for C$_{34}$H$_{39}$N$_5$O$_4$.1.59CF$_3$COOH.0.27H$_2$O C, 58.17; H, 5.40; N, 9.13 Found: C, 58.17; H, 5.40; N, 9.30

EXAMPLE 8

[S-(R*,R*)]-(2-(3H-Imidazol-4-yl)-1-{methyl-[3-methyl-1-(2-methyl-2-phenyl- propylcarbamoyl)-butyl]-carbamoyl}-ethyl)-carbamic Acid Benzyl Ester Step 1: Boc-NMe-Leu-NH-CH$_2$-C(CH$_3$)$_2$-phenyl or (S)-Methyl-[3-methyl-1-(2- methyl-2-phenyl-propylcarbamoyl)-butyl]-carbamic Acid Tert-butyl Ester Boc-NMe-Leu-OH (1.23 g, 5 mmol) was dissolved in methylene chloride (10 mL). β,β-dimethylphenethylamine hydrochloride (Step 5, Example 3) (1.05 g, 5.5 mmol) was added followed by DIEA (1.7 mL, 9.8 mmol) and HBTU (2.1 g, 5.5 mmol) which was dissolved in CH$_2$Cl$_2$:DMF (1:1, 10 mL). The reaction was stirred overnight at room temperature. The solvent was removed in vacuo. The residue was taken up in ethyl acetate and washed twice with saturated NaHCO$_3$, brine, dried over MgSO$_4$, filtered, and concentrated (2.17 g, 5.5 mmol). The product was used without further purification. NMR confirmed the structure of the product.

Step 2: HNMe-Leu-NH-CH$_2$-C(CH$_3$)$_2$-phenyl trifluoroacetate or (S)-4-Methyl-2-methylamino- pentanoic acid (2-methyl-2-phenyl-propyl)-amide TFA Boc-NMe-Leu-NH-CH$_2$-C(CH$_3$)$_2$-phenyl (from Step 1, 2.17 g, 5.5 mmol) was treated with 25% TFA/CH$_2$Cl$_2$ (25 mL) for 2 hours at room temperature. The solvent was reduced in volume and the residue was added to 1:1 hexanes:diethyl ether, which was stored overnight at −40° C. overnight to precipitate the product. The ether/hexane was decanted and the residue dried in vacuo (1.8 g, 4.6 mmol). The product was used without further purification. NMR confirmed the structure of the product.

Step 3: Cbz-His(Trt)-NMe-Leu-NH-CH$_2$-C(CH$_3$)$_2$-phenyl or [S-(R*,R*)]-[1- {Methyl-[3-methyl-1-(2-methyl-2-phenyl-propylcarbamoyl)-butyl]- carbamoyl}-2-(1-trityl-1H-imidazol-4-yl)-ethyl]-carbamic Acid Benzyl Ester To HNMe-Leu-NH-CH$_2$-C(CH$_3$)$_2$-phenyl trifluoroacetate (from Step 2, 1.8 g, 4.6 mmol) was added Cbz-His-(Trt)-OH (synthesized according to the method in Hudspeth J. P., Kaltenbronn J. S., Repine J. T., Roark W. H., Stier M. A., Renin inhibitors III, U.S. Pat. No. 4,735,933; 1988) (2.7 g, 5.0 mmol) in methylene chloride (15 mL), DIEA (1.75 mL, 10 mmol), and HBTU (2.1 g, 5.5 mmol) in CH$_2$Cl$_2$:DMF (1:1, 10 mL). The reaction was stirred overnight at room temperature. The volume of the solvent was reduced and ethyl acetate (100 mL) and saturated NaHCO$_3$ (100 mL) were added. The organic was separated and washed twice with saturated NaHCO$_3$, brine, dried over MgSO$_4$, filtered, and concentrated to give 4.5 g of product, which was used without further purification. NMR confirmed the structure of the product.

Step 4: Cbz-His-NMe-Leu-NH-CH$_2$-C(CH$_3$)$_2$-phenyl or [S-(R*,R*)]-(2-(3H- Imidazol-4-yl)-1-{methyl-[3-methyl-1-(2-methyl-2-phenyl- propylcarbamoyl)-butyl]-carbamoyl}-ethyl)-carbamic Acid Benzyl Ester Cbz-His(Trt)-NMe-Leu-NH-CH$_2$-C(CH$_3$)$_2$-phenyl (from Step 3, 4.5 g, 4.6 mmol) was treated with 50% TFA/CH$_2$Cl$_2$. After stirring for 2 hours at room temperature, the solvent was reduced in volume and the residue was added to 1:1 hexanes:diethyl ether, which was stored overnight at −40° C. to precipitate the product. The ether/hexane was decanted and the residue dried in vacuo. Purification was carried out by reverse-phase preparative HPLC (C-18 reverse-phase column, 20% to 60% of 0.1% TFA in acetonitrile against 0.1% TFA in water, 100 minutes, 13 mL/min) to give the desired product (0.098 g, 0.18 mmol); MS-APCI 549 (m+1).

CHN: Calculated for C$_{31}$H$_{40}$N$_5$O$_4$·1.06CF$_3$COOH·0.89H$_2$O C, 58.21; H, 6.32; N, 10.25 Found: 58.21; H, 6.32; N, 10.15

PFT Inhibitory Activity

The protein:farnesyl transferase (PFT) or farnesyl protein transferase (FPT) inhibitory activity of compounds of the present invention were assayed in HEPES buffer (pH 7.4) containing 5 mM potassium phosphate and 20 µM ZnCl$_2$. The solution also contained 5 mM DTT (dithiothreitol), 5 mM MgCl$_2$, and 0.1% PEG 8000. Assays were performed in 96-well plates (Wallec) and employed solutions composed of varying concentrations of a compound of the present invention in 100% DMSO (dimethylsulfoxide). Upon addition of both substrates, radiolabeled farnesyl pyrophosphate ([1$^3$H], specific activity 15 to 30 Ci/mmol, final concentration 134 nM) and (biotinyl)-Ahe-Thr-Lys-Cys-Val-Ile-Met ([3aS[3a alpha, 4 beta, 6a alpha]-hexahydro-2-oxo-1H-thieno[3,4-d]imidazole-5-pentanoic acid]-[7-aminoheptanoic acid]-Thr-Lys-Cys-Val-Ile-Met) (Ahe is 7-amino-heptanoic acid, Thr is threonine, Lys is lysine, Cys is cysteine, Val is valine, Ile is isoleucine and Met is methionine) (final concentration 0.2 µM), the enzyme reaction was started by addition of SF9 affinity purified rat farnesyl protein transferase. After incubation at 30° C. for 30 minutes, the reaction was terminated by diluting the reaction 2.5-fold with a stop buffer containing 1.5M magnesium acetate, 0.2M H$_3$PO$_4$, 0.5% BSA (bovine serum albumin), and strepavidin beads (Amersham) at a concentration of 1.3 mg/mL. After allowing the plate to settle for 30 minutes at room temperature, radioactivity was quantitated on a micro-Beta counter (Model 1450, Wallec). The assay was also carried out without 5 mM potassium phosphate.

Gel Shift Assay

Twenty-four hours after planting 2×10$^6$ ras-transformed cells per treatment condition, the farnesylation inhibitor is added at varying concentrations. Following an 18-hour incubation period, cells are lysed in phosphate-buffered saline containing 1% Triton X-100, 0.5% sodium deoxycholate, and 0.1% SDS (sodium dodecyl sulfate), pH 7.4 in the presence of several protease inhibitors (PMSF (phenylmethylsulfonylfluoride), antipain, leupeptin, pepstatin A, and aprotinin all at 1 µg/mL). Ras protein is immunoprecipitated from the supernatants by the addition of 3 µg v-H-ras Ab-2 (Y13-259 antibody from Oncogene Science). After overnight immunoprecipitation, 30 µL of a 50% protein G-Sepharose slurry (Pharmacia) is added followed by 45-minute incubation. Pellets are resuspended in 2× triglycine loading buffer (Novex) containing 5% β-mercaptoethanol and then denatured by 5 minutes boiling prior to electrophoresis on 14% Tri-glycine SDS gels. Using Western transfer techniques, proteins are transferred to nitrocellulose membranes followed by blocking in blocking buffer. Upon overnight incubation with primary antibody (pan-ras Ab-2 from Oncogene Science), an antimouse HRP (horse radish peroxidase) conjugate secondary antibody (Amersham) is employed for detection of the ras protein. Blots are developed using ECL (enhanced chemiluminescence) techniques (Amersham).

Clonogenic Assay (6 Well Plates)

Sometime previous to setting up an actual test:

1. Make up 1.5% Bacto Agar in Milli-Q water and autoclave.

2. Make up 500 mL 2× DMEM-HG without phenol red by combining the following:
   1 bottle DMEM base powder (Sigma D-5030)
   4.5 g glucose
   3.7 g sodium bicarbonate
   0.11 g sodium pyruvate
   20 mL of 200 mM L-glutamine (Sigma G-7513)
   1 mL pen-strep (GibcoBRL No. 15140-023)

Adjust pH to 7.1 with HCl; Filter Sterilize

1. Set up makeshift water bath (beaker of water with thermometer, on hot plate) in the hood. Keep water temperature between 37° C. to 43° C.

2. Autoclave 1.5% Bacto Agar for approximately 2 minutes on high, or until completely melted. Then let it cool somewhat before using it. (You can keep it from resolidifying by setting the bottle on the hot plate.)

| 3. | Bottom Layer (0.6% agar) | Top Layer (0.3% agar) |
|---|---|---|
| | 20% calf serum | 20% calf serum |
| | 40% 2X DMEM | 50% 2X DMEM |
| | 40% Bacto Agar (1.5%) | 20% Bacto Agar (1.5%) |
| | | 10% sterile H$_2$O × µL cell suspension |
| | | (to = 5000 cells/well) (H61 cells: NIH transformed 3T3 H-ras cells) |

Depending on the volume of each layer needed, use either 50 mL conical tubes or 200 mL turnip tubes which can be floated in the "water bath".

4. Add 1 mL of bottom layer agar/medium to each well; deliver 1 mL warm agar/medium to a well; then using the tip of the pipet, spread the agar/medium around to completely cover the bottom. Repeat with next well. Do not add the last mL in the pipet to a well, it leads to bubbles.

5. Allow the plates to set at room temperature for about 5 minutes until the bottom layer solidifies.

6. Label sterile Falcon 2054 (12×75 mm) tubes and add appropriate volume of drug solutions into them.

7. Aliquot 4 µL of DMSO or drug solution per 1 mL of agar/medium to appropriate tubes; then add the agar/ medium/cells to each tube. Always add 1 mL more than will actually be needed. Mix up and down in the pipet (gently); then deliver 1 mL to the center of each well. The upper layer is less viscous, so it will generally spread out over the bottom layer unaided. If necessary, rotate the plane of the plate gently to spread the top layer evenly over the bottom layer.

8. Let plates set for 5 or 10 minutes at room temperature to solidify, then put into 5% $CO_2$, 37° C. incubator.

9. On Day 13, add 0.5 mL of INT (tetrazolium 1 mg/mL in Milli-Q $H_2O$, filter sterilized) and return plates to incubator.

10. Count colonies.

The data in the table below shows farnesyl protein transferase inhibitory activity, and activity in the gel shift and clonogenic assays against ras protein of compounds of the present invention.

Example 1 was shown to have submicromolar activity as a ras farnesyl transferase inhibitor, and at a concentration of 1 μM, it was able to inhibit ras protein farnesylation (H-ras-transformed HIH 3T3 cells). Modification at the C-terminus led unexpectedly to increased activity: replacement of the 2-(phenylmethoxy)-ethylamine moiety with phenethylamine (Example 2), led to a 10-fold increase in activity against the enzyme and to a 5-fold increase in cellular activity. Also this modification led to an increase in the inhibition of colony formation (clonogenic assay, H-ras transformed NIH 3T3 cells) from an $IC_{50}$ value of 15.1 μM, for Example 1, compared to an $IC_{50}$ value of 0.58 μM, for the compound exemplified in Example 2. By further modifying the C-terminus of the compound in Example 2 (Example 3), it was possible to unexpectedly increase the activity for the inhibition of ras farnesylation in cells to 0.05 μM, and in the clonogenic assay an $IC_{50}$ value of 0.10 μM was obtained. Modifications at the N-terminus and N-substituted glycine positions, were also carried out, and these analogues have also been shown to be unexpectedly superior as inhibitors of ras farnesyl transferase.

|  | $IC_{50}$ (μM) | | | |
| --- | --- | --- | --- | --- |
| Example | Hepes | 5 mM $PO_4^{-2}$ Hepes | Gel Shift (μM) M.E.D* | Soft Agar $IC_{50}$ (μM) |
| 1 | 7 | 0.4 | 1 | 15.1 |
| 2 | 1.4 | 0.032 | 0.2 | 0.58 |
| 3 | 0.31 | 0.007 | 0.05 | 0.10 |
| 4 | 0.38 | 0.006 | ≦0.05 | |
| 5 | 0.012 | 0.008 | ≦0.05 | |
| 6 | 1.01 | 0.013 | ≦0.05 | |
| 7 | 0.26 | 0.005 | ≦0.05 | |
| 8 | 1.76 | 0.010 | ≦0.05 | |

*MED is minimal effective dose to observe inhibition of ras farnesylation

What is claimed is:

1. Farnesyl protein transferase inhibitory compounds having the Formula 1

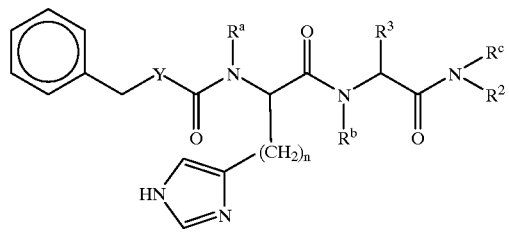

wherein:

$R^a$, $R^b$, $R^c$ are each independently $C_1$-$C_6$ alkyl or hydrogen;

$R^d$, and $R^f$ are each independently $C_1$-$C_6$ alkyl, hydrogen, or phenyl;

Y is —O—, —NH—, or —N($C_1$-$C_6$ alkyl)—;

$R^3$ is —$(CH_2)_n$-phenyl, —$(CH_2)_n$-(phenyl-O-benzyl), —$(CH_2)_n$-$C_1$-$C_6$ alkyl, —$(CH_2)_n$-(phenyl-O-$(CH_2)_n$-heteroaryl), or —$(CH_2)_n$-substituted phenyl;

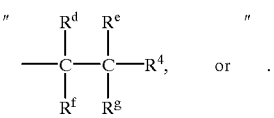

$R^4$ is aryl, substituted aryl, or $C_1$-$C_6$ alkyl; and each n is independently 0 to 5, m is 2 to 4 and the pharmaceutically acceptable salts, and prodrugs thereof.

2. A compound according to claim 1 wherein Y is —O—.

3. A compound according to claim 1 wherein Y is —NH— or —N(CH$_3$)—.

4. A compound according to claim 1 wherein $R^a$ is hydrogen, $R^b$ is methyl, and $R^c$ is hydrogen.

5. A compound according to claim 1 wherein

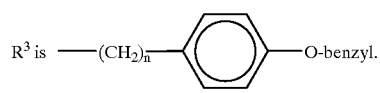

6. A compound according to claim 1 wherein $R^3$ is

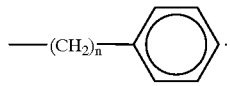

7. A compound according to claim 1 wherein

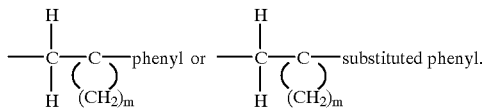

8. A compound according to claim 7 wherein m is 3 or 4

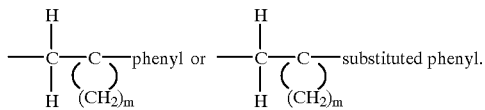

m is 3 or 4.

9. A compound according to claim 1 wherein $R^3$ is —$(CH_2)_n$-$C_1$-$C_6$ alkyl.

10. A compound according to claim 1 wherein

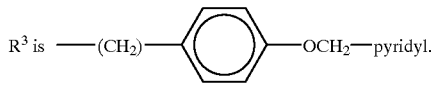

11. The farnesyl protein transferase inhibitory compound: [S-(R*,R*)]-[1-{[2-(4-Benzyloxy-phenyl)-1-[(1-phenyl-cyclobutylmethyl)-carbamoyl]-ethyl}-methyl-carbamoyl)-2-(3H-imidazol- 4-yl)-ethyl]-carbamic acid benzyl ester.

12. The farnesyl protein transferase inhibitory compound: [S-(R*,R*)]-[1-({2-(4-Benzyloxy-phenyl)-1-[(1-phenyl-cyclopropyl-methyl)-carbamoyl]-ethyl}-methyl-carbamoyl)-2-(3H- imidazol-4-yl)-ethyl]-carbamic acid benzyl ester.

13. A composition that comprises a compound of claim 1 together with a carrier.

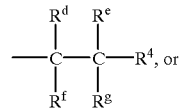

* * * * *

UNITED STATES PATENT AND TRADEMARK OFFICE
CERTIFICATE OF CORRECTION

PATENT NO.   : 6,265,382 B1
DATED        : July 24, 2001
INVENTOR(S)  : Annette Marina Doherty et al.

It is certified that error appears in the above-identified patent and that said Letters Patent is hereby corrected as shown below:

<u>Column 33,</u>
Line 66, "Farnesyl protein transferase inhibitory compounds having the Formula 1" should read -- A Farnesyl protein transferase inhibitory compound having the Formula I --

<u>Column 34,</u>
Line 20, $R_d$ and $R_f$

Column 35, line 10, "A Compound according to claim 1 wherein

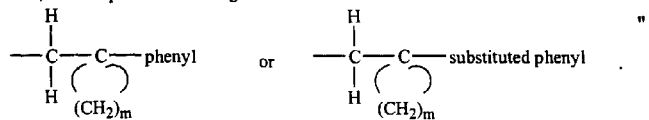

"

should read -- A compound according to claim 1 wherein R2 is

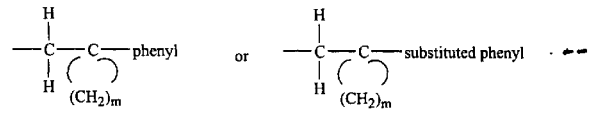

--

UNITED STATES PATENT AND TRADEMARK OFFICE
CERTIFICATE OF CORRECTION

PATENT NO.   : 6,265,382 B1
DATED        : July 24, 2001
INVENTOR(S)  : Annette Marina Doherty et al.

It is certified that error appears in the above-identified patent and that said Letters Patent is hereby corrected as shown below:

Column 35, line 20, " A compound according to claim 7 wherein m is 3 or 4

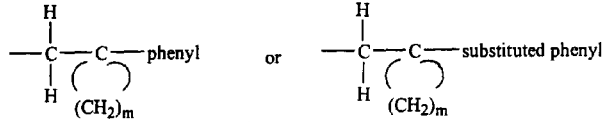

m is 3 or 4."

Column 36, line 20, " delete

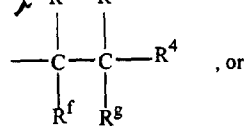

, or               "

Signed and Sealed this

Fifteenth Day of April, 2003

JAMES E. ROGAN
*Director of the United States Patent and Trademark Office*